United States Patent [19]
Godfrey et al.

[11] Patent Number: 5,821,332
[45] Date of Patent: Oct. 13, 1998

[54] RECEPTOR ON THE SURFACE OF ACTIVATED CD4+ T-CELLS: ACT-4

[75] Inventors: Wayne Godfrey, Woodside; David Buck, Half Moon Bay; Edgar G. Engleman, Atherton, all of Calif.

[73] Assignee: The Board of Trustees of the Leland Stanford Junior University, Palo Alto, Calif.

[21] Appl. No.: 147,784

[22] Filed: Nov. 3, 1993

[51] Int. Cl.⁶ .................. C07K 14/705; C07K 14/00; C07K 7/00

[52] U.S. Cl. .................. 530/350; 530/300; 530/324; 530/325; 530/326; 530/327; 530/328; 530/329; 530/330

[58] Field of Search .................. 530/350, 300, 530/324, 325, 326, 327, 328, 329, 330; 435/69.1, 172.3

[56] References Cited

U.S. PATENT DOCUMENTS 5,457,035 10/1995 Baum et al. .................. 435/69.5

FOREIGN PATENT DOCUMENTS 15076 12/1990 WIPO .................. C07K 15/28
11870 7/1992 WIPO .................. A61K 39/395

OTHER PUBLICATIONS

Rentrop, O., et al. "Biochemical analysis of the Workshop antibodies of the Activation Section", *Leukocyte Typing IV. White Cell Differentiation Antigens* (e.d. W. Knapp, Oxford U. Press, 1989) pp. 473.

Vilella, R., et al., "Sequential appearance of the activation antigens", *Leukocyte Typing IV . White Cell Differentiation Antigens* (e.d. W. Knapp, Oxford U. Press, 1989) pp. 495, 497.

Aversa, G., et al., "Activation panel antigen expression on PBL activated by PHA or in MLR", *Leukocyte Typing IV . White Cell Differentiation Antigens* (e.d. W. Knapp, Oxford U. Press, 1989) pp. 498, 500.

King, P., et al. "Tonsillar dendritic–cell–induced T–lymphocyte proliferation: analysis of molecular mechanisms using the activation panel of mAb", *Leukocyte Typing IV . White Cell Differentiation Antigens* (e.d. W. Knapp, Oxford U. Press, 1989) pp. 503, 505.

Young et al. 1983. PNAS USA 80:1194–8.

Mehra et al. 1986. PNAS USA 83:7013–7.

Marston. 1986. Biochem. J. 240: 1–12.

Flanagan et al. 1990. Cell 63:185–94.

Bowie et al. 1990. Science 247: 1306–10.

Bazan, "Emerging families of cytokines and receptors," *Current Biology* 3(9):603–606 (1993).

Knapp et al., "Leukocyte Typing IV. White cell differentiation antigens" (Oxford U. Press, 1989) pp. 391, 396, 398, 409, 461, 474, 475, 477, 482, 485, 487, 488, 496, 501, 504.

Godfrey et al., "Molecular cloning of a cDNA encoding the human homolog of the rat OX–40 antigen," *Tissue Antigens* Abst. (Oct. 1993).

Mallet et al., "Characterization of the MRC OX40 antigen of activated CD4 positive T lymphocytes—a molecule related to nerve growth factor receptor," *EMBO J.* 9(4):1063–1068 (1990).

(List continued on next page.)

*Primary Examiner*—Elizabeth C. Kemmerer
*Attorney, Agent, or Firm*—Walter H. Dreger; Mark T. Kresnak

[57] ABSTRACT

The invention provides purified ACT-4 receptor polypeptides, antibodies against these polypeptides and nucleic acids encoding ACT-4 receptor polypeptides. Also provided are methods of diagnosis and treatment using the same. ACT-4 receptors are preferentially expressed on the surface of activated CD4+ T-cells. ACT-4 receptors are usually expressed at low levels on the surface of activated CD8+ cells, and are usually substantially absent on resting T-cells, and on monocytes and B-cells (resting or activated). An exemplary ACT-4 receptor, termed ACT-4-h-1, has a signal sequence, an extracellular domain comprising three disulfide-bonded intrachain loops, a transmembrane domain, and an intracellular domain.

7 Claims, 9 Drawing Sheets

OTHER PUBLICATIONS

Mallet et al., "A new superfamily of cell surface proteins related to the nerve growth factor receptor," *Immunology Today* 12:220–222 (1990).

Miura et al., "Molecular cloning and characterization of a noval glycoprotein, gp34, that is specifically induced by the human T–cell leukemia virus type I transactivator p40$^{tax}$," *Mol. and Cell. Biol.* 11(3):1313–1325 (1991).

Picker et al., "control of lymphocyte recirculation in man. I. Differential regulation of the peripheral lymph node homing receptor L–selectin on T cells during the virgin to memory cell transition," *J. of Immunology* 150(3): 1105–1121.

Picker et al., "Control of lymphocyte recirculation in man. II. Differential regulation of the cutaneous lymphocyte–associated antigen, a tissue–selective homing receptor for skin–homing T cells," *J. of Immunology* 150(3):1122–1136 (1993).

Tanaka et al., "A glycoprotein antigen detected with new monoclonal antibodies on the surface of human lymphocytes infected with human T–cell leukemia virus type–I (HTLV–I)," *Int. J. Cancer* 36:549–555 (1985).

Tozawa et al., "Species–dependent antigencity of the 34–kDa glycoprotein found on the membrane of various primate lymphocytes transformed by human T–cell leukemia virus type–I (HTLV–I and simian T–cell leukemia virus (STLV–I)," *Int. J. Cancer* 41:231–238 (1988).

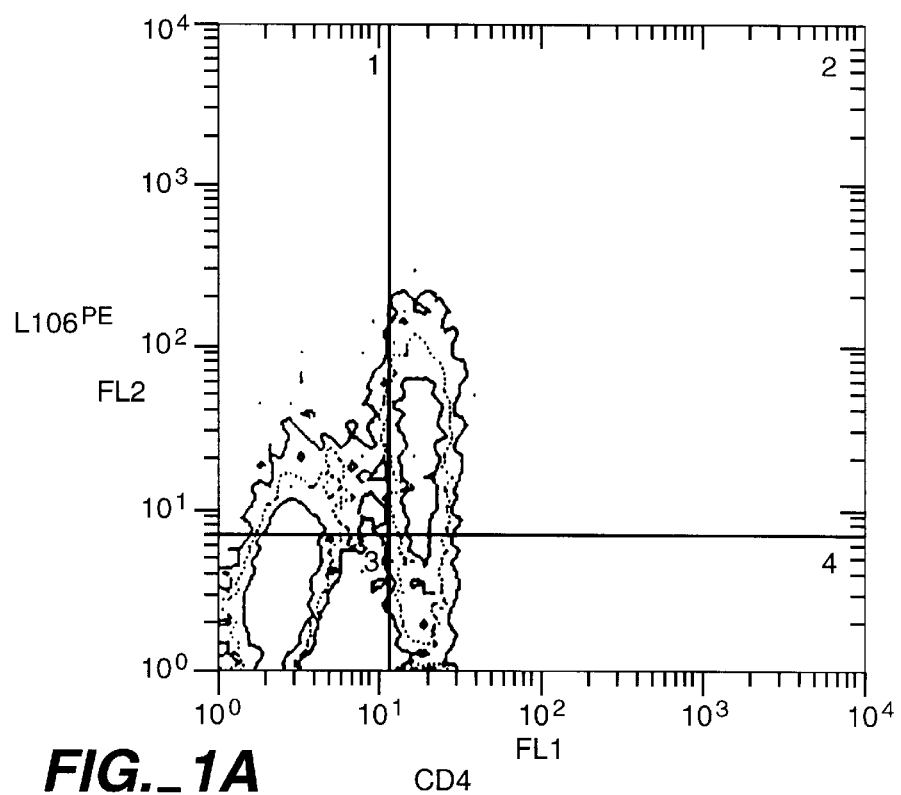
FIG._1A
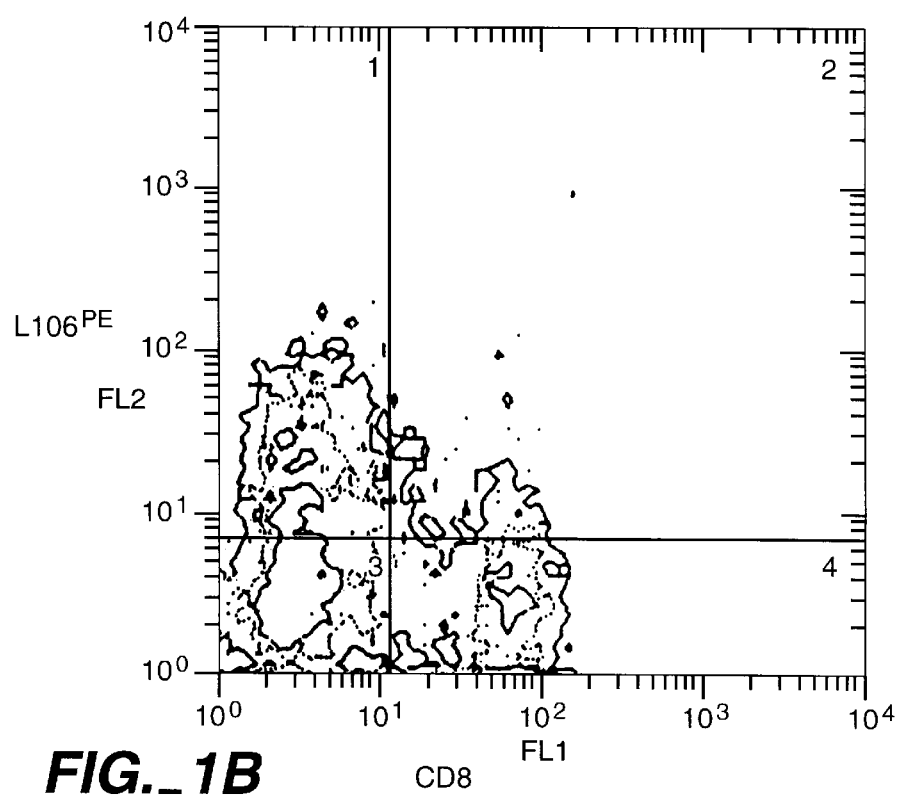
FIG._1B

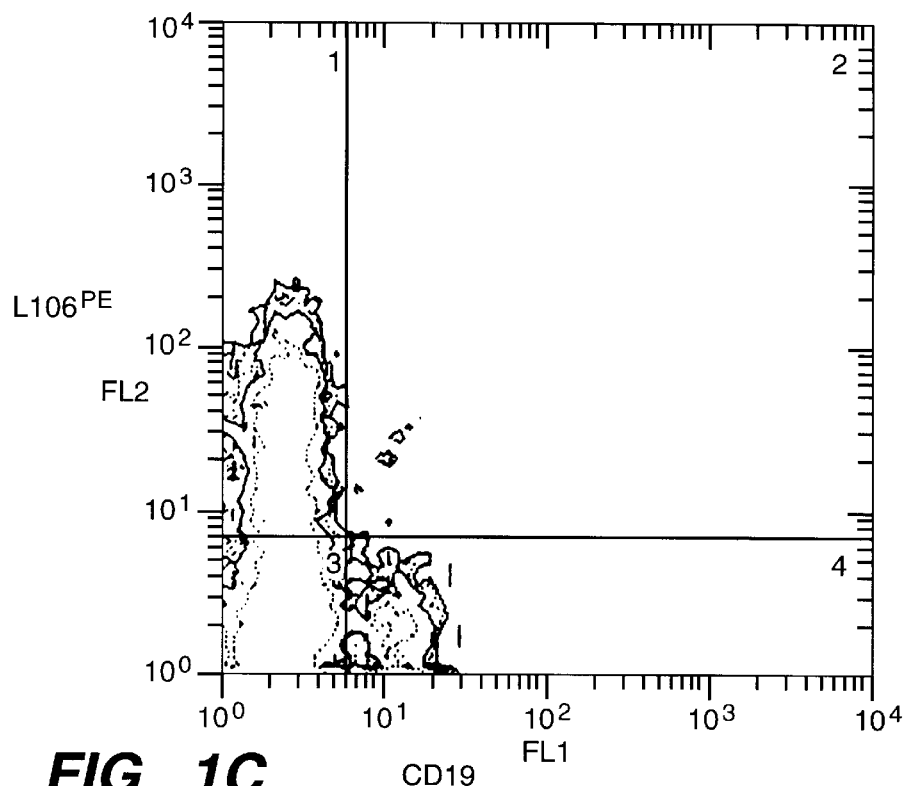
FIG._1C
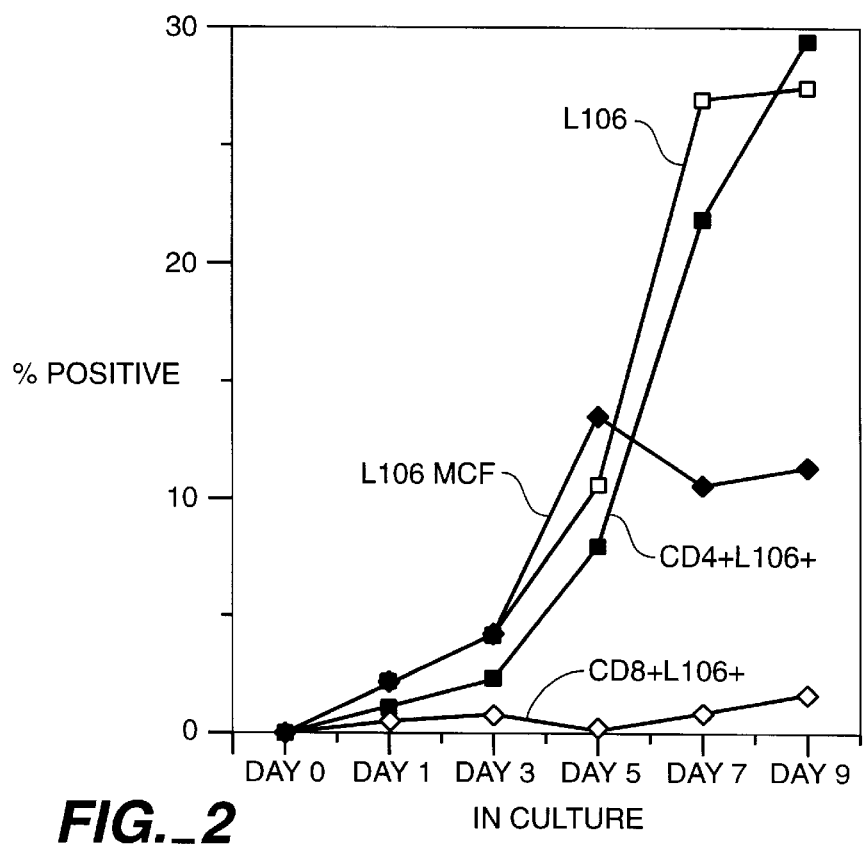
FIG._2

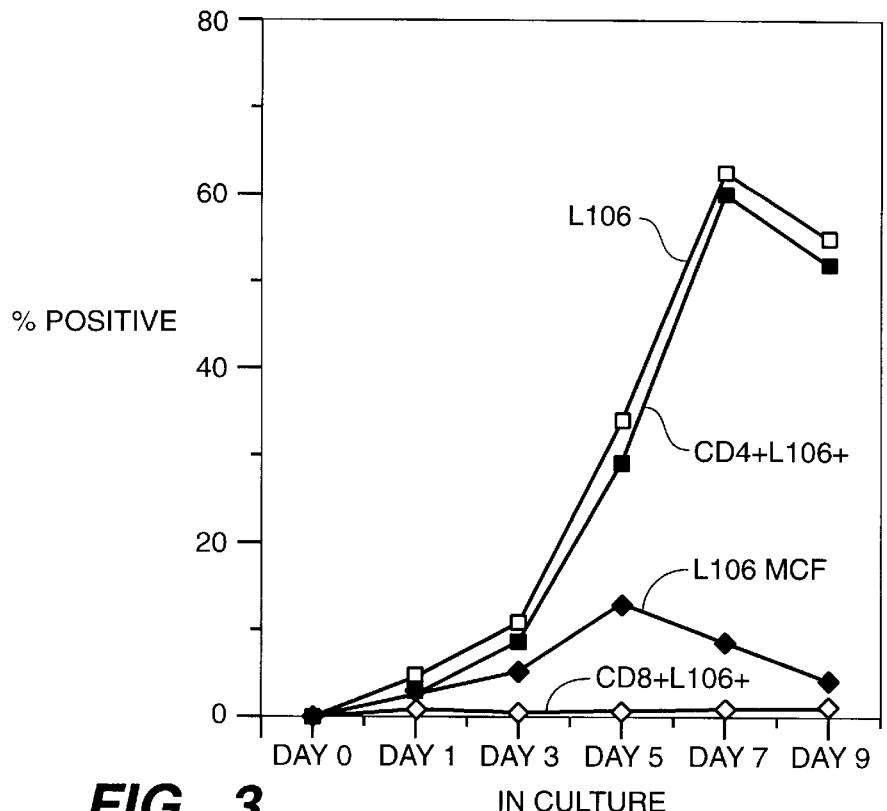
FIG._3
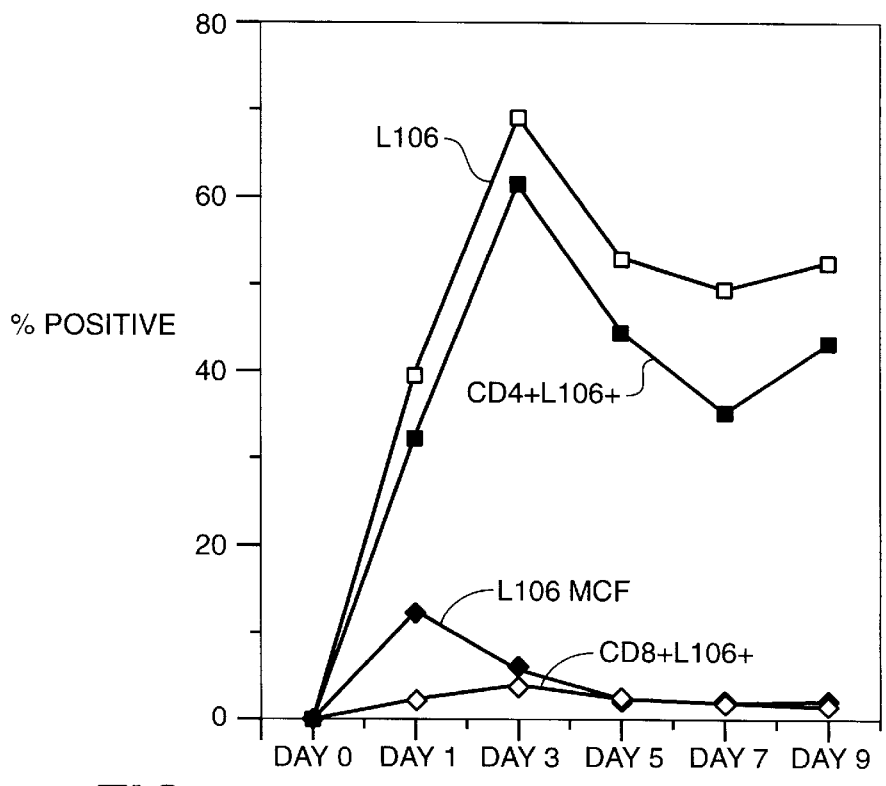
FIG._4

```
                                      27                                          54
      CA GCA GAG ACG AGG ATG TGC GTG GGG GCT CGG CGG CTG GGC CGC GGG CCG TGT
                            M   C   V   G   A   R   R   L   G   R   G   P   C
                                                    SIGNAL SEQUENCE
                                     135                                         162
      GTC GGG GAC ACC TAC CCC AGC AAC GAC CGG TGC TGC CAC GAG TGC AGG CCA GGC
       V   G   D   T   Y   P   S   N   D   R   C   C   H   E   C   R   P   G 243                                         270
      GGG CCG GGC TTC TAC AAC GAC GTG GTC AGC TCC AAG CCG TGC AAG CCC TGC ACG
       G   P   G   F   Y   N   D   V   V   S   S   K   P   C   K   P   C   T 351                                         378
      GAC ACA GTC TGC CGC TGC CGG GCG GGC ACC CAG CCC CTG GAC AGC TAC AAG CCT
       D   T   V   C   R   C   R   A   G   T   Q   P   L   D   S   Y   K   P 459                                         486
      GCC TGC AAG CCC TGG ACC AAC TGC ACC TTG GCT GGG AAG CAC ACC CTG CAG CCG
       A   C   K   P   W   T  |N   C   T|  L   A   G   K   H   T   L   Q   P
                                     GLY
                                     567                                         594
      CCC CAG GAG ACC CAG GGC CCC CCG GCC AGG CCC ATC ACT GTC CAG CCC ACT GAA
       P   Q   E   T   Q   G   P   P   A   R   P   I   T   V   Q   P   T   E 675                                         702
      GGC CGT|GCG GTT GCC GCC ATC CTG GGC CTG GGC CTG GTG CTG GGG CTG CTG GGC
       G   R |A   V   A   A   I   L   G   L   G   L   V   L   G   L   L   G
                                                                              TM
                                     783                                         810
      CCC GAT GCC CAC AAG CCC CCT GGG GGA GGC AGT TTC CGG ACC CCC ATC CAA GAG
       P   D   A   H   K   P   P   G   G   G   S   F   R   T   P   I   Q   E 891                                         918
      GTG GAC GCT GGG CCC CGC CAG GCT GGA GCC CGG AGG GTC TGC TGG GCG AGC AGG 999                                        1026
      AGG TGC CGA TGG CTG CCT CCG GCT CTC TGC TTA CGT ATG CCA TGC ATA CCT CCT
```

*FIG._5A*

```
                                           81                                                      108
GCG GCT CTG CTC CTC CTG GGC CTG GGG CTG AGC ACC GTG ACG GGG CTC CAC TGT
 A   A   L   L   L   L   G   L   G   L   S   T   V   T   G   L   H   C    31
        ─────────────────SIGNAL SEQUENCE───────↑       ↑ CLEAVAGE
                                          189                                                      216
AAC GGG ATG GTG AGC CGC TGC AGC CGC TCC CAG AAC ACG GTG TGC CGT CCG TGC
 N   G   M   V   S   R   C   S   R   S   Q   N   T   V   C   R   P   C    67

297                                                      324
TGG TGT AAC CTC AGA AGT GGG AGT GAG CGG AAG CAG CTG TGC ACG GCC ACA CAG
 W   C   N   L   R   S   G   S   E   R   K   Q   L   C   T   A   T   Q   103

405                                                      432
GGA GTT GAC TGT GCC CCC TGC CCT CCA GGG CAC TTC TCC CCA GGC GAC AAC CAG
 G   V   D   C   A   P   C   P   P   G   H   F   S   P   G   D   N   Q   139

513                                                      540
GCC AGC AAT AGC TCG GAC GCA ATC TGT GAG GAC AGG GAC CCC CCA GCC ACG CAG
 A   S  |N   S   S|  D   A   I   C   E   D   R   D   P   P   A   T   Q   175
        GLY 621                                                      648
GCC TGG CCC AGA ACC TCA CAG GGA CCC TCC ACC CGG CCC GTG GAG GTC CCC GGG
 A   W   P   R   T   S   Q   G   P   S   T   R   P   V   E   V   P   G   211

729                                                      756
┌─────────────────────────────────────────────────────┐
│CCC CTG GCC ATC CTG CTG GCC CTG TAC CTG CTC│CGG AGG GAC CAG AGG CTG CCC
│ P   L   A   I   L   L   A   L   Y   L   L │ R   R   D   Q   R   L   P   247
└─────────────────────────────────────────────────────┘
        TM
                                          837                                                      864
GAG CAG GCC GAC GCC CAC TCC ACC CTG GCC AAG ATC TGA CCT GGG CCC ACC AAG
 E   Q   A   D   A   H   S   T   L   A   K   I   *                       278
                                                    STOP
                                          945                                                      972
GCA GGT GCA GGC CGC CTG CCC CGC CAC GCT CCT GGG CCA ACT CTG CAC CGT TCT

1053
GCC CCG CGG GAC CAC AAT AAA AAC CTT GGC AG
                    POLY-A
```

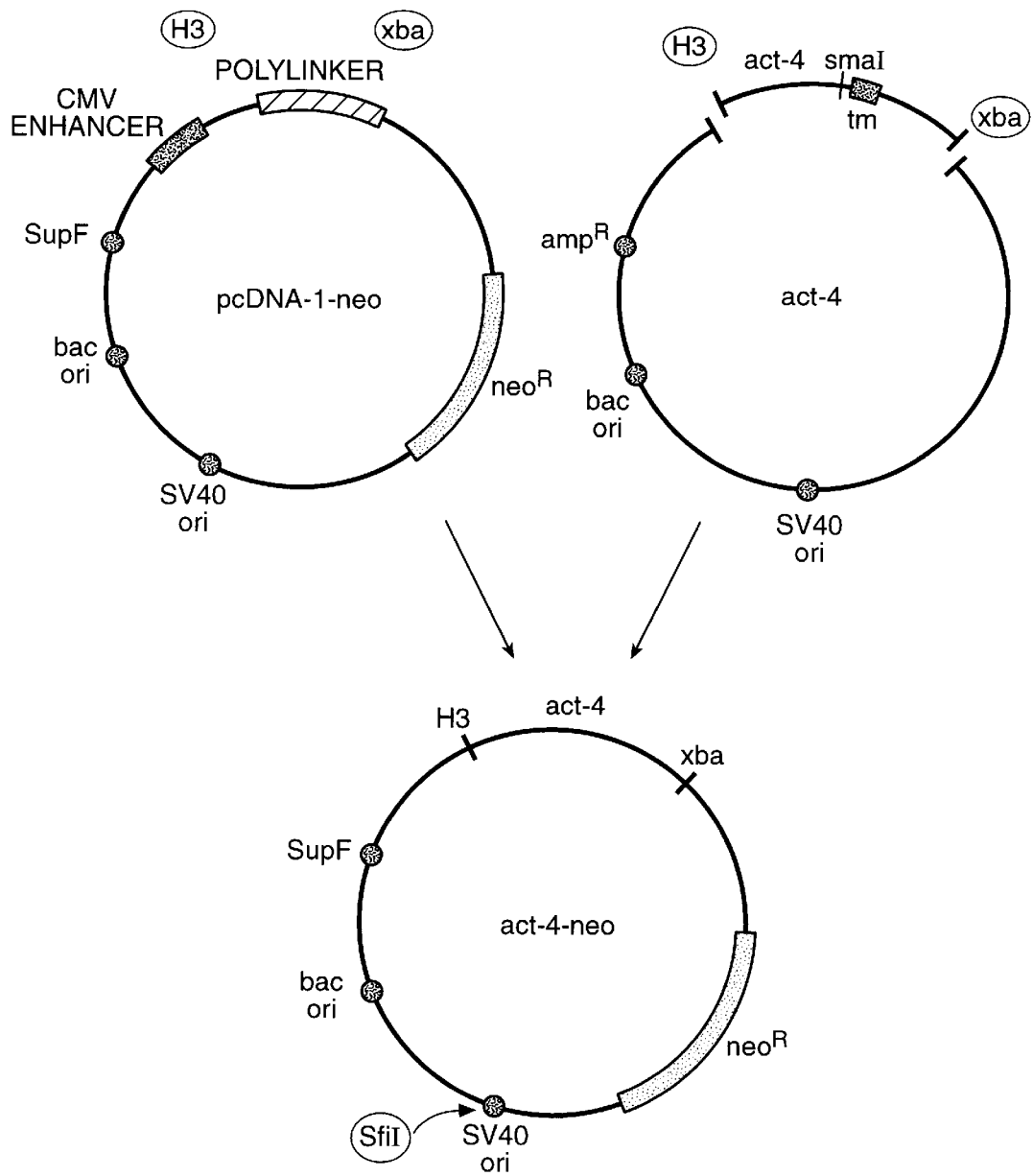
FIG._6

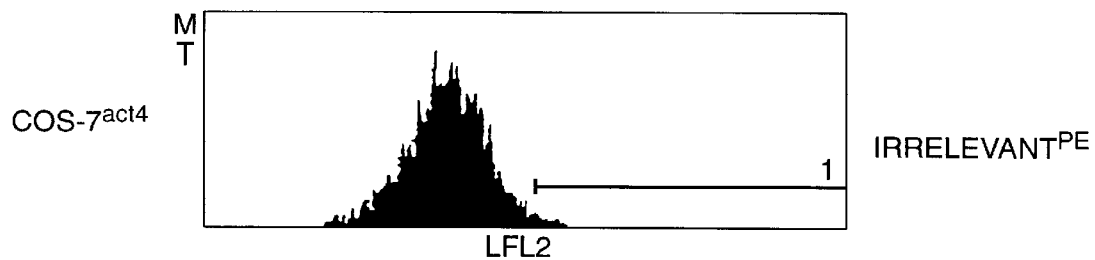
FIG._7A
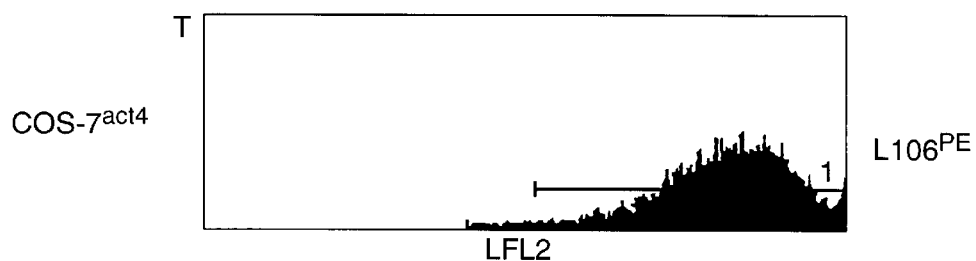
FIG._7B
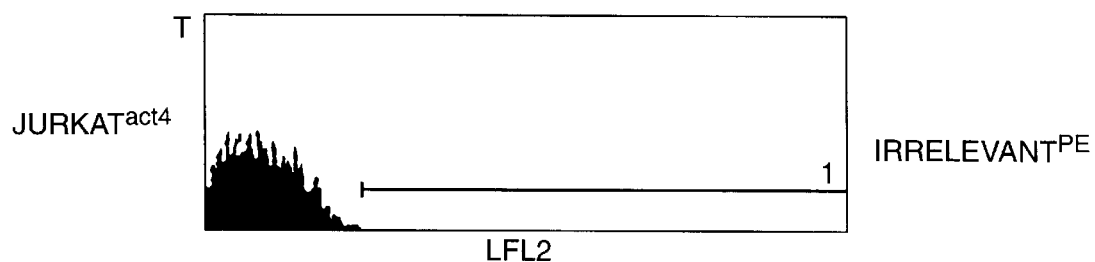
FIG._7C

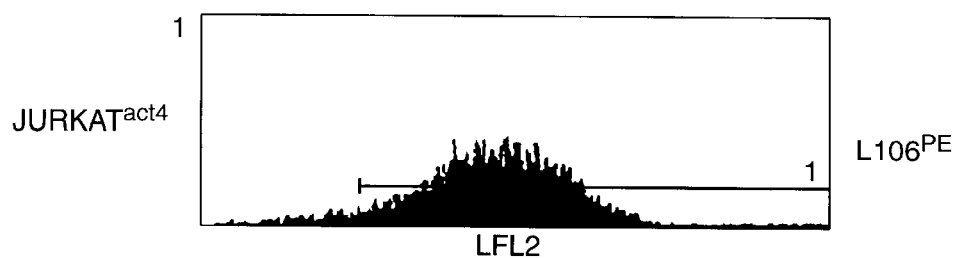
FIG._7D
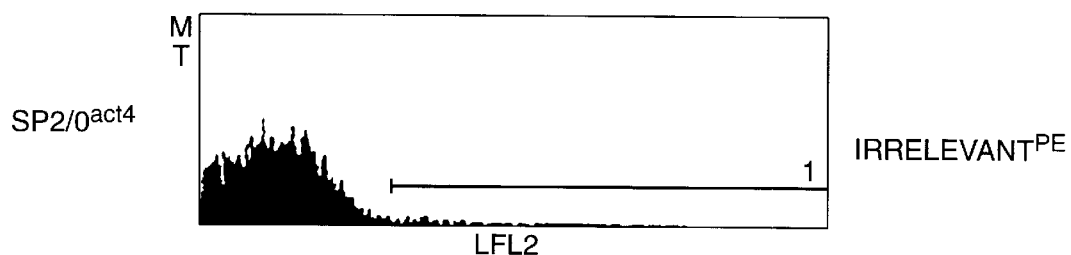
FIG._7E
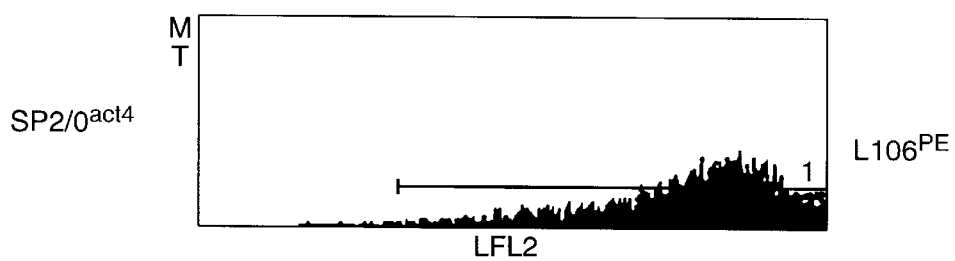
FIG._7F
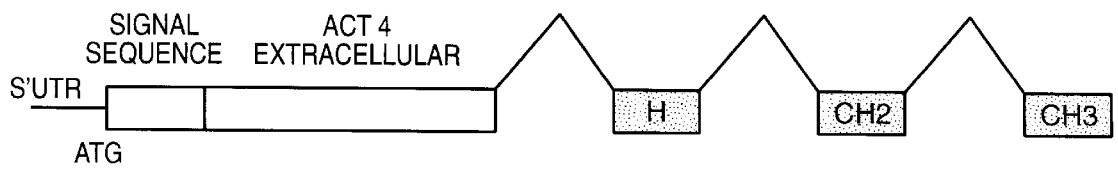
FIG._9

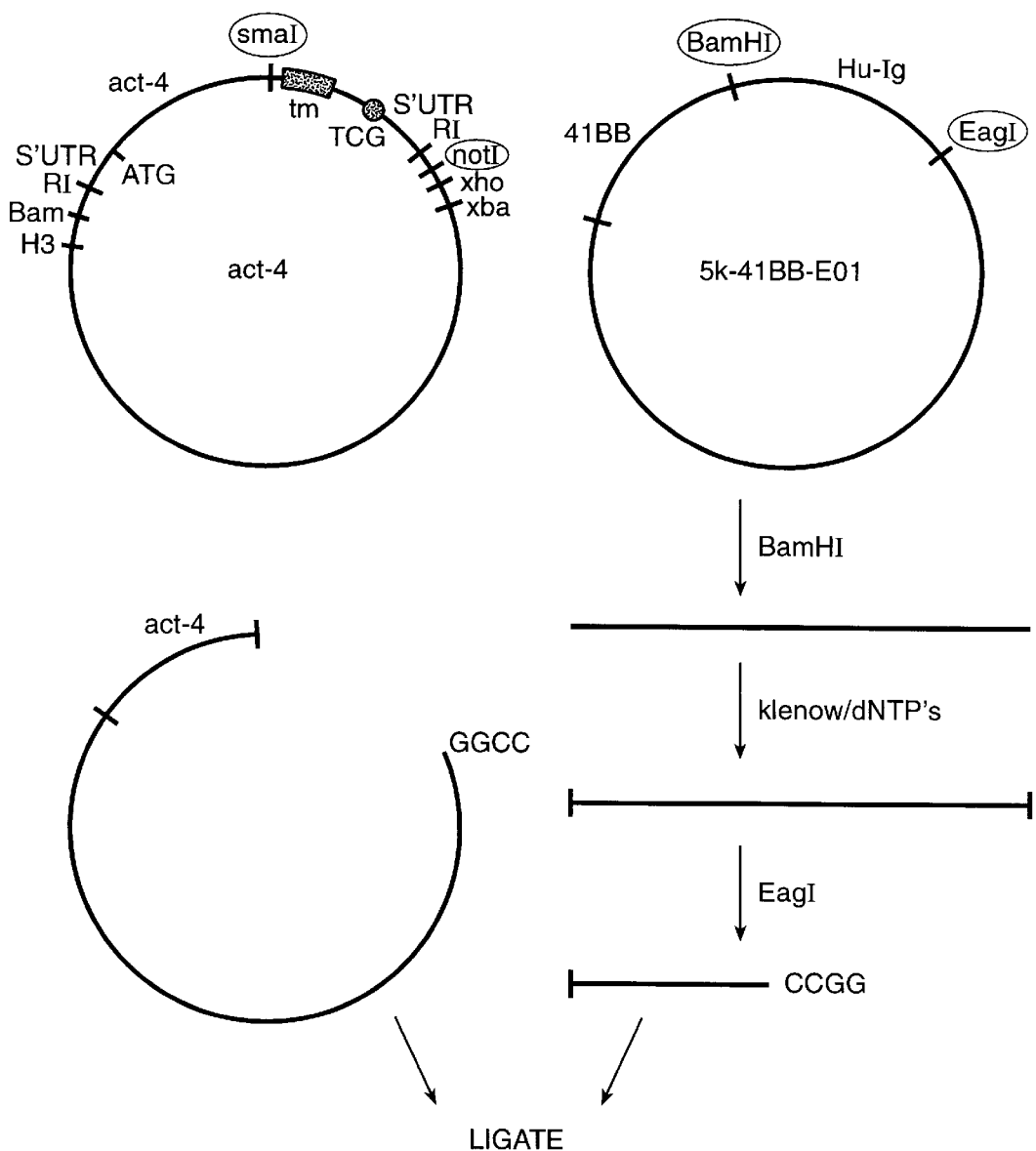
FIG._8

RECEPTOR ON THE SURFACE OF ACTIVATED CD4+ T-CELLS: ACT-4

This invention was made with Government support under contract CA24607 awarded by the National Institutes of Health. The Government has certain rights in this invention.

TECHNICAL FIELD

This invention relates generally to the isolation and characterization of a cell-surface receptor, termed ACT-4, and antibodies thereto, and the use of the antigen and antibodies for monitoring and/or modulating immune responses.

BACKGROUND OF THE INVENTION

Immune responses are largely mediated by a diverse collection of peripheral blood cells termed leukocytes. The leukocytes include lymphocytes, granulocytes and monocytes. Granulocytes are further subdivided into neutrophils, eosinophils and basophils. Lymphocytes are further subdivided into T and B lymphocytes. T-lymphocytes originate from lymphocytic-committed stem cells of the embryo. Differentiation occurs in the thymus and proceeds through prothymocyte, cortical thymocyte and medullary thymocyte intermediate stages, to produce various types of mature T-cells. These subtypes include $CD8^+$ T cells (also known as cytotoxic/suppressor T cells), which, when activated, have the capacity to lyse target cells, and $CD4^+$ T cells (also known as T helper and T inducer cells), which, when activated, have the capacity to stimulate other immune system cell types.

Immune system responses are elicited in several differing situations. The most frequent response is as a desirable protection against infectious microorganisms. However, undesired immune response can occur following transplantation of foreign tissue, or in an autoimmune disease, in which one of a body's own antigens is the target for the immune response. Immune responses can also be initiated in vitro by mitogens or antibodies against certain receptors. In each of these situations, an immune response is transduced from a stimulating event via a complex interaction of leukocytic cell types. However, the participating cell types and nature of the interaction between cell types may vary for different stimulating events. For example, immune responses against invading bacteria are often transduced by formation of complexes between an MHC Class II receptor and a bacterial antigen, which then activate $CD4^+$ T-cells. By contrast, immune responses against viral infections are principally transduced by formation of MHC Class I/viral antigen complexes and subsequent activation of $CD8^+$ cells.

Over recent years, many leukocyte cell surface antigens have been identified, some of which have been shown to have a role in signal transduction. It has been found that signals may be transduced between a cell-surface receptor and either a soluble ligand or a cell-surface-bound ligand. The amino acid sequences of leukocyte surface molecules comprise a number of characteristic recurring sequences or motifs. These motifs are predicted to be related in evolution, have similar folding patterns and mediate similar types of interactions. A number of superfamilies, including the immunoglobulin and nerve growth factor receptor superfamilies, have been described. Members of the nerve growth factor receptor family include NGFR, found on neural cells; the B-cell antigen CD40; the rat OX-40 antigen, found on activated $CD4^+$ cells (Mallet et al., EMBO J. 9:1063–1068 (1990) (hereby incorporated by reference for all purposes); two receptors for tumor necrosis factor (TNF), LTNFR-1 and TNFR-II, found on a variety of cell types; 4-1BB found on T-cells; SFV-T2, an open reading frame in Shope fibroma virus; and possibly fas, CD27 and CD30. See generally Mallet & Barclay, *Immunology Today* 12:220–222 (1990) (hereby incorporated by reference for all purposes).

The identification of cell-surface receptors has suggested new agents for suppressing undesirable immune responses such as transplant rejection, autoimmune disease and inflammation. Agents, particularly antibodies, that block receptors of immune cells from binding to soluble molecules or cell-bound receptors can impair immune responses. Ideally, an agent should block only undesired immune responses (e.g., transplant rejection) while leaving a residual capacity to effect desirable responses (e.g., responsive to pathogenic microorganisms). The immunosuppressive action of some agents, for example, antibodies against the CD3 receptor and the IL-2 receptor have already been tested in clinical trials. Although some trials have shown encouraging results, significant problems remain. First, a patient may develop an immune response toward the blocking agent preventing continued immunosuppressive effects unless different agents are available. Second, cells expressing the target antigen may be able to adapt to the presence of the blocking agent by ceasing to express the antigen, while retaining immune functions. In this situation, continued treatment with a single immunosuppressive agent is ineffective. Third, many targets for therapeutic agents are located on more than one leukocyte subtype, with the result that it is generally not possible to selectively block or eliminate the response of only specific cellular subtypes and thereby leave unimpaired a residual immune capacity for combating infectious microorganisms.

Based on the foregoing it is apparent that a need exists for additional and improved agents capable of suppressing immune responses, particularly agents capable of selective suppression. The present invention fulfills these and other needs, in part, by providing a cellular receptor localized on activated human $CD4^+$ T-lymphocytes.

SUMMARY OF THE INVENTION

In one embodiment of the invention, purified ACT-4 receptor polypeptides are provided. The amino acid sequence of one such polypeptide, termed ACT-4-h-1, is shown in FIG. 5. ACT-4 receptor polypeptides typically exhibit at least 80% amino acid sequence identity to the ACT-4-h-1 amino acid sequence. The polypeptides usually comprise at least one, and sometimes all of the following domains: a signal sequence, an intracellular domain, a transmembrane domain and an extracellular domain. Many polypeptides are characterized by their presence on activated $CD4^+$ T-cells and their substantial absence on resting T-cells. Some full-length polypeptides have a molecular weight of about 50 kDa before deglycosylation and about 27 kDa thereafter.

The invention also provides extracellular domains of ACT-4 receptor polypeptides. The extracellular domains typically comprise at least one disulfide-bonded loop and sometimes three such loops. The extracellular domains are usually soluble and capable of specific binding to an ACT-4 ligand. Sometimes an extracellular domain is fused to a second polypeptide such as a constant region of an immunoglobulin heavy chain. Some extracellular domains consist essentially of an epitope specifically bound by an antibody designated L106.

In another aspect of the invention, antibodies that specifically bind to an ACT-4-h-1 receptor polypeptide are provided. The antibodies are usually monoclonal antibodies. One example of such an antibody is designated L106. Some antibodies inhibit activation of CD4$^+$ T-cells, whereas other antibodies stimulate activation of these cells. Some antibodies of the invention compete with the L106 antibody for specific binding to an ACT-4-h-1 receptor polypeptide, and most of these antibodies also compete with L106 for specific binding to activated CD4$^+$ T-cells. Other antibodies of the invention specifically bind to a different epitope than that bound by the L106 antibody. Also provided are fragments of the L106 antibody that specifically bind to an ACT-4-h-1 receptor polypeptide.

Also provided are humanized antibodies comprising a humanized heavy chain and a humanized light chain. The humanized light chain comprises three complementarity determining regions (CDR1, CDR2 and CDR3) having amino acid sequences from the corresponding complementarity determining regions of a L106 antibody light chain, and having a variable region framework sequence substantially identical to a human light chain variable region framework sequence. The humanized heavy chain comprises three complementarity determining regions (CDR1, CDR2 and CDR3) having amino acid sequences from the corresponding complementarity determining regions of an L106 antibody heavy chain, and having a variable region framework sequence substantially identical to a human heavy chain variable region framework sequence. The humanized antibodies specifically bind to an ACT-4-h-1 receptor polypeptide with a binding affinity that is within three-fold of the binding affinity of the L106 antibody.

In another aspect, the invention provides nucleic acids fragments encoding the ACT-4 receptor polypeptides discussed supra. An example of such a nucleic acid fragment comprises the nucleotide sequence encoding the ACT-4-h-1 receptor shown in FIG. 5. The nucleic acid fragments typically exhibit at least eighty percent sequence identity to the nucleic acid sequence of FIG. 5.

The invention also provides isolated cell lines containing the nucleic acid fragments discussed supra. The cell lines usually express an ACT-4 receptor polypeptide on their cell surface. Some of the cell lines are stable, as when the nucleic acid fragment is incorporated in the genome of the cell line.

The invention also provides methods of screening for immunosuppressive agents. An ACT-4-h-1 receptor polypeptide is contacted with a potential immunosuppressive agent. Specific binding between the ACT-4-h-1 receptor polypeptide or fragment and the agent is then detected. The existence of specific binding is indicative of immunosuppressive activity.

The invention also provides methods of screening for an ACT-4 ligand. A biological sample containing the ACT-4 ligand is contacted with an ACT-4-h-1 receptor polypeptide. A complex is formed between the ligand and the ACT-4-h-1 receptor polypeptide. The complex is then dissociated to obtain the ligand.

In another aspect, the invention provides methods of suppressing an immune response in a patient suffering from an immune disease or condition. A therapeutically effective dose of a pharmaceutical composition is administered to the patient. The pharmaceutical composition comprises a pharmaceutically active carrier and a monoclonal antibody that specifically binds to an ACT-4-h-1 receptor polypeptide.

Also provided are methods of detecting activated CD4$^+$ T-cells. A tissue sample from a patient is contacted with a monoclonal antibody that specifically binds to an ACT-4-h-1 receptor polypeptide. Specific binding between the monoclonal antibody and the tissue sample is detected. The existence of specific binding reveals the presence of activated CD4$^+$ T-cells. The presence of activated CD4$^+$ T-cells is often diagnostic of a disease or condition of the immune system.

Also provided are methods of inducing an immune response to a selected antigen. A monoclonal antibody that specifically binds to an ACT-4-h-1 receptor polypeptide and that stimulates activation of CD4$^+$ T-cells is administered to a patient. The patient is exposed to the selected antigen.

The invention also provides ACT-4 ligands that specifically bind to an ACT-4-h-1 receptor polypeptide.

BRIEF DESCRIPTION OF THE DRAWINGS

FIG. 1: Two-color staining of peripheral blood lymphocytes to analyze expression of ACT-4-h-1 on different cell types.

FIG. 2: Kinetics of ACT-4-h-1 expression on alloantigen-activated CD4$^+$ T-cells. MCF=Mean channel fluorescence.

FIG. 3: Kinetics of ACT-4-h-1 expression on tetanus-toxoid-activated CD4$^+$ T-cells.

FIG. 4: Kinetics of ACT-4-h-1 expression on PHA-activated CD4$^+$ T-cells.

FIG. 5: cDNA (upper) (SEQ. ID NO:2) and deduced amino acid sequence (lower) (SEQ. ID NO:2) of ACT-4-h-1. The Figure indicates the locations of an N-terminal signal sequence, two possible signal cleavage sites (vertical arrows), two glycosylation sites (gly), a transmembrane domain (TM), a stop codon and a poly-A signal sequence.

FIG. 6: Construction of expression vector for production of stable transfectants expressing ACT-4-h-1.

FIG. 7: FACS™ analysis showing expression of ACT-4-h-1 on stable transfectants of COS-7, Jurkat and SP2/O cell lines.

FIG. 8: Fusion of an ACT-4-h-1 extracellular domain with an immunoglobulin heavy chain constant region to form a recombinant globulin.

FIG. 9: Schematic topographical representation of recombinant globulin formed from fusion of an ACT-4-h-1 extracellular domain with an immunoglobulin heavy chain constant region to form a recombinant globulin.

DEFINITIONS

Abbreviations for the twenty naturally occurring amino acids follow conventional usage (*Immunology—A Synthesis*, (E. S. Golub & D. R. Gren, eds., Sinauer Associates, Sunderland, Mass., 2nd ed., 1991) (hereby incorporated by reference for all purposes). Stereoisomers (e.g., D-amino acids) of the twenty conventional amino acids, unnatural amino acids such as α, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N, N,N-trimethyllysine, ε-N-acetyllysine, o-phosphoserine, N-acetylserine, N-formylmethionine, 3-methylhistidine, 5-hydroxylysine, ω-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The phrase "polynucleotide sequence" refers to a single or double-stranded polymer of deoxyribonucleotide or ribonucleotide bases read from the 5' to the 3' end. It includes self-replicating plasmids, infectious polymers of DNA or RNA and non-functional DNA or RNA.

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence shown in FIG. 5, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith & Waterman, *Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. (USA)* 85:2444 (1988), by computerized implementations of these algorithms (FASTDB (Intelligenetics), BLAST (National Center for Biomedical Information) or GAP, BESTFIT, FASTA, and TFASTA (Wisconsin Genetics Software Package Release 7.0, Genetics Computer Group, 575 Science Dr., Madison, Wis.)), or by inspection, and the best alignment (i.e., resulting in the highest percentage of sequence similarity over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 70, 80 or 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length ACT-4-h-1 sequence shown in FIG. 5.

As applied to polypeptides, the term "substantial identity" means that two peptide sequences, when optimally aligned, such as by the programs BLAZE (Intelligenetics) GAP or BESTFIT using default gap weights, share at least 70 percent or 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "epitope" includes any protein determinant capable of specific binding to an immunoglobulin or T-cell receptor. Specific binding exists when the dissociation constant for antibody binding to an antigen is ≦1 μM, preferably ≦100 nM and most preferably ≦1 nM. Epitopic determinants usually consist of chemically active surface groupings of molecules such as amino acids or sugar side chains and usually have specific three dimensional structural characteristics, as well as specific charge characteristics.

The term "higher cognate variants" as used herein refers to a gene sequence that is evolutionarily and functionally related between humans and higher mammalian species, such as primates, porcines and bovines. The term does not include gene sequences from rodents, such as rats. Thus, the cognate primate gene to the ACT-4-h-1 gene is the primate gene which encodes an expressed protein which has the greatest degree of sequence identity to the ACT-4-h-1 receptor protein and which exhibits an expression pattern similar to that of the ACT-4-h-1 protein (i.e., expressed on activated CD4$^+$ cells).

The term "patient" includes human and veterinary subjects.

DETAILED DESCRIPTION

I. ACT-4 Receptor Polypeptides

According to one embodiment of the invention, receptors on the surface of activated CD4$^+$ T-cells (referred to as ACT-4 receptors) and fragments thereof are provided. The term ACT-4 receptor polypeptide is used generically to encompass full-length receptors and fragments thereof. The amino acid sequence of the first ACT-4 receptor to be characterized [hereinafter ACT-4-h-1] is shown in FIG. 5. The suffix -h designates human origin and the suffix -1 indicates that ACT-4-h-1 is the first ACT-4 receptor to be characterized. The term ACT-4 receptor refers not only to the protein having the sequence shown in FIG. 5, but also to other proteins that represent allelic, nonallelic, and higher cognate variants of ACT-4-h-1, and natural or induced mutants of any of these. Usually, ACT-4 receptor polypeptides will also show substantial sequence identity with the ACT-4-h-1 sequence. Typically, an ACT-4 receptor polypeptide will contain at least 4 and more commonly 5, 6, 7, 10 or 20, 50 or more contiguous amino acids from the ACT-4-h-1 sequence. It is well known in the art that functional domains, such as binding domains or epitopes can be formed from as few as four amino acids residues.

ACT-4 receptor polypeptides will typically exhibit substantial amino acid sequence identity with the amino acid sequence of ACT-4-h-1, and be encoded by nucleotide sequences that exhibit substantial sequence identity with the nucleotide sequence encoding ACT-4-h-1 shown in FIG. 5. The nucleotides encoding ACT-4 receptor proteins will also typically hybridize to the ACT-4-h-1 sequence under stringent conditions. However, these nucleotides will not usually hybridize under stringent conditions to the nucleic acid encoding OX-40 receptor, as described by Mallet et al., *EMBO J.* 9:1063–68 (1990) (hereby incorporated by reference for all purposes) (See particularly FIG. 2A of the Mallet et al. reference). Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and Ph) at which 50% of the target sequence hybridizes to a perfectly matched probe. Typically, stringent conditions will be those in which the salt concentration is at least about 0.02 molar at Ph 7 and the temperature is at least about 60° C. As other factors may significantly affect the stringency of hybridization, including, among others, base composition and size of the complementary strands, the presence of organic solvents and the extent of base mismatching, the combination of parameters is more important than the absolute measure of any one.

Usually, ACT-4 receptor polypeptides will share at least one antigenic determinant in common with ACT-4-h-1 but will not be specifically reactive with antibodies against the rat OX-40 polypeptide. The existence of a common antigenic determinant is evidenced by cross-reactivity of the variant protein with any antibody prepared against ACT-4-h-1 (see Section IV). Cross-reactivity is often tested using polyclonal sera against ACT-4-h-1, but can also be tested using one or more monoclonal antibodies against ACT-4-h-1, such as the antibody designated L106.

Often ACT-4 receptor polypeptides will contain modified polypeptide backbones. Modifications include chemical derivatizations of polypeptides, such as acetylations, carboxylations and the like. They also include glycosylation modifications (N- and O-linked) and processing variants of a typical polypeptide. These processing steps specifically include enzymatic modifications, such as ubiquitinization and phosphorylation. See, e.g., Hershko & Ciechanover, *Ann. Rev. Bioch.* 51:335–364 (1982). The ACT-4-h-1 protein, for example, is heavily modified in that the observed molecular weight is about 50 kDa, whereas the predicted molecular weight based on amino acid sequence is only 27 kDa. Two putative glycosylation sites have been identified in its extracellular domain.

ACT-4 receptors likely share some or all of the topological features found for ACT-4-h-1. The amino acid sequence for ACT-4-h-1 contains a 22 or 24 amino acid putative N-terminal signal sequence. The 24 amino acid sequence is more probably based on the criteria of von Heijne, *Nucleic Acids Res.* 14: 4683–4690 (1986) (incorporated by reference for all purposes). The ACT-4-h-1 receptor contains a single additional hydrophobic stretch of 27 amino acids spanning residues 213–240. The hydrophobic stretch probably corresponds to a transmembrane domain and its existence is consistent with ACT-4-h-1 being a type I integral membrane protein (i.e., having a single transmembrane domain with the N-terminal domain comprising the extracellular region and the C-terminus comprising the intracellular region). The 189 or 191 amino acids (depending on the exact location of the signal cleavage site) of ACT-4-h-1 amino-proximal to the transmembrane segment are designated the extracellular domain, while the 37 amino acids carboxy-proximal to the transmembrane segment are designated the intracellular domain. From the amino-terminus, the extracellular domain has an NH$_2$-terminal hydrophobic putative signal sequence, and three intrachain loops formed by disulfide bonding between paired cysteine residues.

The topological arrangement of ACT-4 receptor polypeptides is similar to that of other members of the nerve growth factor receptor family, particularly to the rat OX-40 receptor. However, the other members show some divergence in the number of extracellular disulfide loops and glycosylation sites and in the size of the intracellular domain. See Mallet & Barclay, supra.

Although not all of the domains discussed above are necessarily present in all ACT-4 receptor polypeptides, an extracellular domain is expected to be present in most. Indeed, in some ACT-4 receptor polypeptides, it is possible that only an extracellular domain is present, and the natural state of such proteins is not as cell-surface bound proteins, but as soluble proteins, for example, dispersed in an extracellular body fluid. The existence of soluble variant forms has been observed for other cell surface receptors, including one member of the nerve growth factor receptor family, SFV-T2. See Mallet & Barclay, supra.

Besides substantially full-length polypeptides, the present invention provides for biologically active fragments of the polypeptides. Significant biological activities include receptor binding, antibody binding (e.g., the fragment competes with an intact ACT-4 receptor for specific binding to an antibody), immunogenicity (i.e., possession of epitopes that stimulate B or T cell responses against the fragment), and agonism or antagonism of the binding of an ACT-4 receptor polypeptide to its ligand. A segment of an ACT-4 receptor protein or a domain thereof will ordinarily comprise at least about 5, 7, 9, 11, 13, 16, 20, 40, or 100 contiguous amino acids.

Segments of ACT-4 receptor polypeptides are often terminated near boundaries of functional or structural domains. Structural and functional domains are identified by comparison of nucleotide and/or amino acid sequence data such as is shown in FIG. 5 to public or proprietary sequence databases. Preferably, computerized comparison methods are used to identify sequence motifs or predicted protein conformation domains that occur in other proteins of known structure and/or function. Structural domains include an intracellular domain, transmembrane domain, and extracellular domain, which is in turn contains three disulfide-bonded loops. Functional domains include an extracellular binding domain through which the ACT-4 receptor polypeptide interacts with external soluble molecules or other cell-bound ligands and an intracellular signal-transducing domain.

Some fragments will contain only extracellular domains, such as one or more disulfide-bonded loops. Such fragments will often retain the binding specificity of an intact ACT-4 receptor polypeptide, but will be soluble rather than membrane bound. Such fragments are useful as competitive inhibitors of ACT-4 receptor binding.

ACT-4 receptors are further identified by their status as members of the nerve growth factor receptor family. The amino acid sequence of ACT-4-h-1 is at least 20% identical to NGF-R, TNF-R, CD40, 4-1BB, and fas/APO1. ACT-4-h-1 exhibits 62% amino acid sequence identity with the rat OX-40 gene, which is also characterized by selective expression on activated $CD4^+$ cells.

ACT-4 receptors are also identified by a characteristic cellular distribution. Most notably, ACT-4 receptors are usually easily detected on activated $CD4^+$ T cells (percent cells expressing usually greater than about 25 or 50% and often about 80%; mean channel fluorescence usually greater than about 10 and often about 20–25, on a Coulter Profile Flow Cytometer after immunofluorescence staining). ACT-4 receptors are usually substantially absent on resting T-cells, B-cells (unless activated with PMA), NK cells, and monocytes (unless activated with PMA). Substantially absent means that the percentage of cells expressing ACT-4 is usually less than about 5%, and more usually less than about 2%, and that the mean channel is usually less than about 4, and more usually less than about 2, measured on a Coulter Profile Flow Cytometer, after immunofluoresence staining of the cells. (See Example 2) ACT-4 receptors are usually expressed at low levels on activated $CD8^+$ cells (percent cells expressing about 4–10%; mean channel fluorescence about 2–4 on a Coulter Profile Flow Cytometer after immunofluoresence staining). The low level of expression observed on $CD8^+$ cells suggests that expression is confined to a subpopulation of $CD8^+$ cells. The expression of ACT-4 receptors on the surface of activated $CD4^+$ cells has been observed for several different mechanisms of activation, including alloantigenic, tetanus toxoid or mitogenic (e.g., PHA) stimuli. Expression peaks after about 7 days of allogantigenic or tetanus toxoid stimulation and after about three days of PHA stimulation. These data indicate that ACT-4 receptors should be classified as early activation antigens that are substantially absent on resting cells. The observation that ACT-4 receptors are preferentially expressed on activated $CD4^+$ cells and are expressed to a much lesser extent on activated $CD8^+$ cells, but are substantially absent on most or all other subtypes of lymphoid cells (except in response to highly nonphysiological stimuli such as PMA) contrasts with the cell type specificity of other activation antigens found on human leukocytes.

The expression of ACT-4 receptors on the surface of activated $CD4^+$ T cells suggests that the receptor has a role in activation of these cells. Such a role is consistent with that of some other members of the nerve growth factor receptor family. For example, CD40 stimulates the G1-S phase transition in B lymphocytes, and nerve growth factor receptor transduces a signal from the cytokine nerve growth factor., which results in neuronal differentiation and survival (Barde, Y-A. *Neuron* 2: 1525–1534 (1989)) (incorporated by reference for all purposes). However, other roles for ACT-4 receptors can also be envisaged, for example, interaction with other lymphoid cell types. The existence of such roles is consistent with the diverse functions of other nerve growth factor receptor family members, such as tumor necrosis factor, whose interaction with tumor necrosis factor receptor can result in inflammation or tumor cell death.

Fragments or analogs comprising substantially one or more functional domain (e.g., an extracellular domain) of ACT-4 receptors can be fused to heterologous polypeptide sequences, such that the resultant fusion protein exhibits the functional property(ies) conferred by the ACT-4 receptor fragment and/or the fusion partner. The orientation of the ACT-4 receptor fragment relative to the fusion partner will depend on experimental considerations such as ease of construction, stability to proteolysis, thermal stability, immunological reactivity, amino- or carboxyl-terminal residue modification, and so forth. Potential fusion partners include chromogenic enzymes such as β-galactosidase, protein A or G, a FLAG protein such as described by Blanar & Rutter, *Science* 256:1014–1018 (1992), toxins (e.g., diphtheria toxin, Psuedonomas ectotoxin A, ricin toxin or phospholipase C) and immunoglobulin components.

Recombinant globulins (Rg) formed by fusion of ACT-4 receptor fragments and immunoglobulin components often have most or all of the physiological properties associated with the constant region of the particular immunoglobulin class used. For example, the recombinant globulins may be capable of fixing complement, mediating antibody dependent cell toxicity, stimulating B cells, or traversing blood vessel walls and entering the interstitial space. The recombinant globulins are usually formed by fusing the C-terminus of an ACT-4 receptor extracellular domain to the N-terminus of the constant region domain of a heavy chain immunoglobulin, thereby simulating the conformation of an authentic immunoglobulin chain. The immunoglobulin chain is preferably of human origin, particularly if the recombinant globulin is intended for therapeutic use. Recombinant globulins are usually soluble and have a number of advantageous properties relative to unmodified ACT-4 receptors. These properties include prolonged serum half-life, the capacity to lyse target cells for which an ACT-4 receptor has affinity, by effector functions, and the capacity to bind molecules such as protein A and G, which can be used to immobilize the recombinant globulin in binding analyses.

II. Methods of Producing Polypeptides

A. Recombinant Technologies

The nucleotide and amino acid sequences of ACT-4-h-1 shown in FIG. 5, and corresponding sequences for other ACT-4 receptor variants obtained as described in Section III, infra, allow production of polypeptides of full-length ACT-4 receptor polypeptides sequences and fragments thereof. Such polypeptides may be produced in prokaryotic or eukaryotic host cells by expression of polynucleotides encoding ACT-4 receptor, or fragments and analogs thereof. The cloned DNA sequences are expressed in hosts after the sequences have been operably linked to (i.e., positioned to ensure the functioning of) an expression control sequence in an expression vector. Expression vectors are typically replicable in the host organisms either as episomes or as an integral part of the host chromosomal DNA. Commonly, expression vectors will contain selection markers, e.g., tetracycline resistance or hygromycin resistance, to permit detection and/or selection of those cells transformed with the desired DNA sequences (see, e.g., U.S. Pat. No. 4,704,362).

E. coli is one prokaryotic host useful for cloning the DNA sequences of the present invention. Other microbial hosts suitable for use include bacilli, such as Bacillus subtilis, and other Enterobacteriaceae, such as Salmonella, Serratia, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. Saccharomyces is a preferred host, with suitable vectors having expression control sequences, such as promoters, including 3-phosphoglycerate kinase or other glycolytic enzymes, and an origin of replication, termination sequences and the like as desired. Insect cells (e.g., SF9) with appropriate vectors, usually derived from baculovirus, are also suitable for expressing ACT-4 receptor or ligand polypeptides. See Luckow, et al. *Bio/Technology* 6:47–55 (1988) (incorporated by reference for all purposes).

Higher eukaryotic mammalian tissue cell culture may also be used to express and produce the polypeptides of the present invention (see Winnacker, From *Genes to Clones* (VCH Publishers, NY, N.Y., 1987)) (incorporated by reference for all purposes). Eukaryotic cells are actually preferred, because a number of suitable host cell lines capable of secreting and authentically modifying human proteins have been developed in the art, and include the CHO cell lines, various COS cell lines, HeLa cells, myeloma cell lines, Jurkat cells, etc. Expression vectors for these cells can include expression control sequences, such as an origin of replication, a promoter (e.g., a HSV tk promoter or pgk (phosphoglycerate kinase) promoter), an enhancer (Queen et al., *Immunol. Rev.* 89:49 (1986)), and necessary processing information sites, such as ribosome binding sites, RNA splice sites, polyadenylation sites (e.g., an SV40 large T Ag poly A addition site), and transcriptional terminator sequences. Preferred expression control sequences are promoters derived from immunoglobulin genes, SV40, adenovirus, bovine papillomavirus, and the like. The vectors containing the DNA segments of interest (e.g., polypeptides encoding an ACT-4 receptor) can be transferred into the host cell by well-known methods, which vary depending on the type of cellular host. For example, $CaCl_2$ transfection is commonly utilized for prokaryotic cells, whereas $CaPO_4$ treatment or electroporation may be used for other cellular hosts. Vectors may exist as episome or integrated into the host chromosome.

B. Naturally Occurring ACT-4 Receptor Proteins

Natural ACT-4 receptor polypeptides are isolated by conventional techniques such as affinity chromatography. For example, polyclonal or monoclonal antibodies are raised against previously-purified ACT-4-h-1 and attached to a suitable affinity column by well known techniques. See, e.g., Hudson & Hay, *Practical Immunology* (Blackwell Scientific Publications, Oxford, UK, 1980), Chapter 8 (incorporated by reference for all purposes). For example, anti-ACT-4-h-1 can be immobilized to a protein-A sepharose column via crosslinking of the $F_c$ domain with a homobifunctional crosslinking agent, such as dimethyl pimelimidate. Cell extracts are then passed through the column, and ACT-4 receptor protein specifically bound by the column, eluted with, for example, 0.5M pyrogenic acid, pH 2.5. Usually, an intact form of ACT-4 receptor is obtained by such isolation techniques. Peptide fragments are generated from intact ACT-4 receptors by chemical (e.g., cyanogen bromide) or enzymatic cleavage (e.g., V8 protease or trypsin) of the intact molecule.

C. Other Methods

Alternatively, ACT-4 receptor polypeptides can be synthesized by chemical methods or produced by in vitro translation systems using a polynucleotide template to direct translation. Methods for chemical synthesis of polypeptides and in vitro translation are well known in the art, and are described further by Berger & Kimmel, *Methods in Enzymology*, Volume 152, *Guide to Molecular Cloning Techniques* Academic Press, Inc., San Diego, Calif., 1987).

III. Nucleic Acids

A. Cloning ACT-4 Receptor Nucleic Acids

Example 5 presents nucleic acid sequence data for a cDNA clone of an ACT-4 receptor designated ACT-4-h-1. The sequence includes both a translated region and 3' and 5' flanking regions. This sequence data can be used to design probes with which to isolate other ACT-4 receptor genes. These genes include the human genomic gene encoding ACT-4-h-1, and cDNAs and genomic clones from higher mammalian species, and allelic and nonallelic variants, and natural and induced mutants of all of these genes. Specifically, all nucleic acid fragments encoding all ACT-4 receptor polypeptides disclosed in this application are provided. Genomic libraries of many species are commercially available (e.g., Clontech, Palo Alto, Calif.), or can be isolated de novo by conventional procedures. cDNA libraries are best prepared from activated $CD4^+$ cells, which express ACT-4-h-1 in large amounts.

The probes used for isolating clones typically comprise a sequence of about at least 24 contiguous nucleotides (or their complement) of the cDNA sequence shown in FIG. 5. For example, a full-length polynucleotide corresponding to the sequence shown in FIG. 5 can be labeled and used as a hybridization probe to isolate genomic clones from a human genomic clone library in e.g., λEMBL4 or λGEM11 (Promega Corporation, Madison, Wis.); typical hybridization conditions for screening plaque lifts (Benton & Davis, Science 196:180 (1978)) can be: 50% formamide, 5×SSC or SSPE, 1–5×Denhardt's solution, 0.1–1% SDS, 100–200 µg sheared heterologous DNA or tRNA, 0–10% dextran sulfate, $1\times10^5$ to $1\times10^7$ cpm/ml of denatured probe with a specific activity of about $1\times10^8$ cpm/µg, and incubation at 42° C. for about 6–36 hours. Prehybridization conditions are essentially identical except that probe is not included and incubation time is typically reduced. Washing conditions are typically 1–3×SSC, 0.1–1% SDS, 50°–70° C. with change of wash solution at about 5–30 minutes. Hybridization and washing conditions are typically less stringent for isolation of higher cognate or nonallelic variants than for e.g., the human genomic clone of ACT-4-h-1.

Alternatively, probes can be used to clone ACT-4 receptor genes by methods employing the polymerase chain reaction (PCR). Methods for PCR amplification are described in e.g., *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19:4967 (1991); Eckert, K. A. and Kunkel, T. A., *PCR Methods and Applications* 1:17 (1991); *PCR* (eds. McPherson et al., IRL Press, Oxford); and U.S. Pat. No. 4,683,202 (each of which is incorporated by reference for all purposes).

Alternatively, synthetic polynucleotide sequences corresponding to all or part of the sequences shown in FIG. 5 may be constructed by chemical synthesis of oligonucleotides.

Nucleotide substitutions, deletions, and additions can be incorporated into the polynucleotides of the invention. Nucleotide sequence variation may result from degeneracy of the genetic code, from sequence polymorphisms of various ACT-4 receptor alleles, minor sequencing errors, or may be introduced by random mutagenesis of the encoding nucleic acids using irradiation or exposure to EMS, or by changes engineered by site-specific mutagenesis or other techniques of modern molecular biology. See Sambrook et al., *Molecular Cloning: A Laboratory Manual* (C.S.H.P. Press, NY 2d ed., 1989) (incorporated by reference for all purposes). For nucleotide sequence that are capable of being transcribed and translated to produce a functional polypeptide, degeneracy of the genetic code results in a number of nucleotide sequences that encode the same polypeptide. The invention includes all such sequences. Generally, nucleotide substitutions, deletions, and additions should not substantially disrupt the ability of an ACT-4 receptor polynucleotide to hybridize to the sequence of ACT-4-h-1 shown in FIG. 5 under stringent conditions. Typically, ACT-4 receptor polynucleotides comprise at least 25 consecutive nucleotides which are substantially identical to a naturally-occurring ACT-4 receptor sequence (e.g., FIG. 5), more usually ACT-4 receptor polynucleotides comprise at least 50 to 100 consecutive nucleotides, which are substantially identical to a naturally-occurring ACT-4 receptor sequence.

ACT-4 receptor polynucleotides can be short oligonucleotides (e.g., about 10, 15, 25, 50 or 100 contiguous bases from the ACT-h-1 sequence shown in FIG. 5), such as for use as hybridization probes and PCR (or LCR) primers. ACT-4 receptor polynucleotide sequences can also comprise part of a larger polynucleotide that includes sequences that facilitate transcription (expression sequences) and translation of the coding sequences, such that the encoded polypeptide product is produced. Construction of such polynucleotides is well known in the art and is described further in Sambrook et al., supra (C.S.H.P. Press, NY 2d ed. 1989). The ACT-4 receptor polynucleotide can be fused in frame with another polynucleotide sequence encoding a different protein (e.g., glutathione S-transferase, β-galactosidase or an immunoglobulin $F_c$ domain) for encoding expression of a fusion protein (see, e.g., Byrn et al., *Nature*, 344:667–670 (1990)) (incorporated by reference for all purposes).

IV, Antibodies and Hybridomas

In another embodiment of the invention, antibodies against ACT-4 receptors and to their ligands (see Section V) are provided.

A. General Characteristics of Antibodies

Antibodies or immunoglobulins are typically composed of four covalently bound peptide chains. For example, an IgG antibody has two light chains and two heavy chains. Each light chain is covalently bound to a heavy chain. In turn each heavy chain is covalently linked to the other to form a "Y" configuration, also known as an immunoglobulin conformation. Fragments of these molecules, or even heavy or light chains alone, may bind antigen. Antibodies, fragments of antibodies, and individual chains are also referred to herein as immunoglobulins.

A normal antibody heavy or light chain has an N-terminal ($NH_2$) variable (v) region, and a C-terminal (—COOH) constant (C) region. The heavy chain variable region is referred to as $V_H$ (including, for example, $V_\gamma$), and the light chain variable region is referred to as $V_L$ (including $V_K$ or $V_\lambda$). The variable region is the part of the molecule that binds to the antibody's cognate antigen, while the Fc region (the second and third domains of the C region) determines the antibody's effector function (e.g., complement fixation, opsonization). Full-length immunoglobulin or antibody "light chains" (generally about 25 kDa, about 214 amino acids) are encoded by a variable region gene at the N-terminus (generally about 110 amino acids) and a κ (kappa) or λ (lambda) constant region gene at the COOH-terminus. Full-length immunoglobulin or antibody "heavy chains" (generally about 50 Kd, about 446 amino acids), are similarly encoded by a variable region gene (generally encoding about 116 amino acids) and one of the constant region genes, e.g., gamma (encoding about 330 amino acids). Typically, the "$V_L$" Will include the portion of the light chain encoded by the $V_L$ and/or $J_L$ (J or joining region) gene segments, and the "$V_H$" will include the portion of the heavy chain encoded by the $V_H$, and/or $D_H$ (D or diversity region) and $J_H$ gene segments. See, generally, Roitt et al., *Immunology* (2d ed. 1989), Chapter 6 and Paul, *Fundamental Immunology* (Raven Press, 2d ed., 1989) (each of which is incorporated by reference for all purposes).

An immunoglobulin light or heavy chain variable region consists of a "framework" region interrupted by three hypervariable regions, also called complementarity-determining regions or CDRs. The extent of the framework region and CDRs have been defined (see Kabat et al. (1987), "Sequences of Proteins of Immunological Interest," U.S. Department of Health and Human Services; Chothia et al., *J. Mol. Biol.* 196:901–917 (1987) (each of which is incorporated by reference for all purposes). The sequences of the framework regions of different light or heavy chains are relatively conserved within a species. The framework region of an antibody, that is the combined framework regions of the constituent light and heavy chains, serves to position and align the CDRs in three dimensional space. The CDRs are primarily responsible for binding to an epitope of an antigen. The CDRs are typically referred to as CDR1, CDR2, and CDR3, numbered sequentially starting from the N-terminus.

The constant region of the heavy chain molecule, also known as $C_H$, determines the isotype of the antibody. Antibodies are referred to as IgM, IgD, IgG, IgA, and IgE depending on the heavy chain isotype. The isotypes are encoded in the mu ($\mu$), delta ($\Delta$), gamma ($\gamma$), alpha ($\alpha$), and epsilon ($\epsilon$) segments of the heavy chain constant region, respectively. In addition, there are a number of $\gamma$ subtypes. There are two types of light chains, $\kappa$ and $\lambda$. The determinants of these subtypes typically reside in the constant region of the light chain, also referred to as the $C_L$ in general, and $C_\kappa$ or $C_\lambda$ in particular.

The heavy chain isotypes determine different effector functions of the antibody, such as opsonization or complement fixation. In addition, the heavy chain isotype determines the secreted form of the antibody. Secreted IgG, IgD, and IgE isotypes are typically found in single unit or monomeric form. Secreted IgM isotype is found in pentameric form; secreted IgA can be found in both monomeric and dimeric form.

B. Production of Antibodies

Antibodies which bind either an ACT-4 receptor, a ligand thereto, or binding fragments of either, can be produced by a variety of means. The production of non-human monoclonal antibodies, e.g., murine, rat and so forth, is well known and may be accomplished by, for example, immunizing the animal with a preparation containing an ACT-4 receptor or its ligands, or an immunogenic fragment of either of these. Particularly, useful as immunogens are cells stably transfected with recombinant ACT-4 receptor genes and expressing ACT-4 receptors on their cell surface. Antibody-producing cells obtained from the immunized animals are immortalized and screened for the production of an antibody which binds to ACT-4 receptors or their ligands. See Harlow & Lane, *Antibodies, A Laboratory Manual* (C.S.H.P. NY, 1988) (incorporated by reference for all purposes).

Several techniques for generation of human monoclonal antibodies have also been described but are generally more onerous than murine techniques and not applicable to all antigens. See, e.g., Larrick et al., U.S. Pat. No. 5,001,065, for review (incorporated by reference for all purposes). One technique that has successfully been used to generate human monoclonal antibodies against a variety of antigens is the trioma methodology of Ostberg et al. (1983), *Hybridoma* 2:361–367, Ostberg, U.S. Pat. No. 4,634,664, and Engleman et al., U.S. Pat. No. 4,634,666 (incorporated by reference for all purposes). The antibody-producing cell lines obtained by this method are called triomas, because they are descended from three cells—two human and one mouse. Triomas have been found to produce antibody more stably than ordinary hybridomas made from human cells.

An alternative approach is the generation of humanized immunoglobulins by linking the CDR regions of non-human antibodies to human constant regions by recombinant DNA techniques. See Queen et al., *Proc. Natl. Acad. Sci. USA* 86:10029–10033 (1989) and WO 90/07861 (incorporated by reference for all purposes). The humanized immunoglobulins have variable region framework residues substantially from a human immunoglobulin (termed an acceptor immunoglobulin) and complementarity determining regions substantially from a mouse immunoglobulin, e.g., the L106 antibody (referred to as the donor immunoglobulin). The constant region(s), if present, are also substantially from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See Carter et al., WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine L106 variable region framework residue and a selected human variable region framework residue, the human framework amino acid should usually be substituted by the equivalent framework amino acid from the mouse antibody when it is reasonably expected that the amino acid:

(1) noncovalently binds antigen directly, (2) is adjacent to a CDR region, (3) otherwise interacts with a CDR region (e.g. is within about 3A of a CDR region), or (3) participates in the VL-VH interface.

Other candidates for substitution are acceptor human framework amino acids that are unusual for a human immunoglobulin at that position. These amino acids can be substituted with amino acids from the equivalent position of the L106 antibody or from the equivalent positions of more typical human immunoglobulins.

A further approach for isolating DNA sequences which encode a human monoclonal antibody or a binding fragment thereof is by screening a DNA library from human B cells according to the general protocol outlined by Huse et al., *Science* 246:1275–1281 (1989) and then cloning and amplifying the sequences which encode the antibody (or binding fragment) of the desired specificity. The protocol described by Huse is rendered more efficient in combination with phage display technology. See, e.g., Dower et al., WO 91/17271 and McCafferty et al., WO 92/01047. Phage display technology can also be used to mutagenize CDR regions of antibodies previously shown to have affinity for ACT-4 receptors or their ligands. Antibodies having improved binding affinity are selected.

Anti-ACT-4 receptor antibodies that specifically bind to the same epitope as the L106 antibody are usually identified by a competitive binding assay. The assay has three components, an ACT-4 polypeptide (e.g., ACT-4-h-1), L106 antibody, which is usually labelled, and the antibody under test. Often the ACT-4 receptor polypeptide is immobilized to a solid support. The test antibody binds to the same epitope as the L106 antibody if it reduces the amount of L106 antibody that specifically binds to the ACT-4 receptor polypeptide. The extent of screening necessary to obtain such antibodies can be reduced by generating antibodies with a protocol in which the specific epitope bound by L106 is used as an immunogen. Antibodies binding to the same epitope as L106 may exhibit a substantially, but not completely, identical amino acid sequence to the L106 antibody, or may have an unrelated primary structure to the L106 antibody.

Anti-ACT-4 receptor antibodies having a different binding specificity than L106 (i.e., which bind to a different epitope) are identified by a complementary approach. Test antibodies are screened for failure to compete with the L106 antibody for binding to an ACT-4 receptor polypeptide. The extent of screening can be reduced by generating antibodies with a protocol in which a fragment lacking a specific epitope bound by L106 is used as an immunogen.

Antibodies having the capacity to stimulate or inhibit activation of $CD4^+$ cells can be identified by the screening procedures discussed in Section VI, infra. Some antibodies may selectively inhibit activation in response to some stimuli (e.g., alloantigenic but not mitogenic, or vice versa), and not to others. Some antibodies' inhibitory capacity may depend on the time after activation at which the antibody is added. Some antibodies may have the capacity to activate $CD4^+$ cells independently of other stimuli, whereas other anti-ACT-4 receptor antibodies may only have the capacity to augment the efficacy of another stimulus such as that provided by PHA.

Antibodies isolated by the above procedures can be used to generate anti-idiotypic antibodies by, for example, immunization of an animal with the primary antibody. For anti-ACT-4 receptor antibodies, anti-idiotype antibodies whose binding to the primary antibody is inhibited by ACT-4 receptors or fragments thereof are selected. Because both the anti-idiotypic antibody and the ACT-4 receptors or fragments thereof bind the primary immunoglobulin, the anti-idiotypic immunoglobulin may represent the "internal image" of an epitope and thus may substitute for the ACT-4 ligand.

C. Epitope Mapping

The epitope bound by the L106 or any other anti-ACT-4 receptor antibody is determined by providing a family of fragments containing different amino acid segments from an ACT-4 receptor polypeptide, such as ACT-4-h-1. Each fragment typically comprises at least 4, 6, 8, 10, 20, 50 or 100 contiguous amino acids. Collectively, the family of polypeptide covers much or all of the amino acid sequence of a full-length ACT-4 receptor polypeptide. Members of the family are tested individually for binding to e.g., the L106 antibody. The smallest fragment that can specifically bind to the antibody under test delineates the amino acid sequence of the epitope recognized by the antibody.

D. Fragments of Antibodies, and Immunotoxins

In another embodiment of the invention, fragments of antibodies against ACT-4 receptors or their ligands are provided. Typically, these fragments exhibit specific binding to the ACT-4 receptor with an affinity of at least $10^7 M$, and more typically $10^8$ or $10^9 M$. Antibody fragments include separate heavy chains, light chains Fab, Fab' F(ab')$_2$, Fabc, and Fv. Fragments are produced by recombinant DNA techniques, or by enzymic or chemical separation of intact immunoglobulins.

In another embodiment, immunotoxins are provided. An immunotoxin is a chimeric compound consisting of a toxin linked to an antibody having a desired specificity. The antibody serves as a targeting agent for the toxin. See generally Pastan et al., *Cell* 47:641–648 (1986). A toxin moiety is couple to an intact antibody or a fragment thereof by chemical or recombinant DNA techniques. Preferably, the toxin is linked to an immunoglobulin chain in the form of a contiguous protein. See, e.g. Chovnick et al., *Cancer Res.* 51:465; Chaudhary et al., *Nature* 339:394 (1989) (incorporated by reference for all purposes). Examples of suitable toxin components are listed in Section I, supra, and are reviewed in e.g., *The Specificity and Action of Animal, Bacterial and Plant Toxins* (ed. P. Cuatrecasas, Chapman Hall, London, 1976) (incorporated by reference for all purposes).

E. Hybridomas and Other Cell Lines

All hybridomas, triomas and other cell lines producing the antibodies and their fragments discussed, supra, are expressly included in the invention. These include the hybridoma line HBL106, deposited as ATCC HB 11483, (at the American Type Culture Collection, 12301 Parklawn Drive, Rockville, Md. 20852, on 3 Nov. 1993), which produces the L106 mouse antibody.

F. Uses of Antibodies

Anti-ACT-4 receptor antibodies and their binding fragments are useful for screening cDNA expression libraries, preferably containing human or primate cDNA derived from various tissues and for identifying clones containing cDNA inserts, which encode structurally-related, immunocrossreactive proteins. See Aruffo & Seed, *Proc. Natl. Acad. Sci. USA* 84:8573–8577 (1987) (incorporated by reference for all purposes). Antibodies are also useful to identify and/or purify immunocrossreactive proteins that are structurally or evolutionarily related to the native ACT-4 receptor polypeptides or to fragments thereof used to generate the antibody. Antibodies against ACT-4 ligands are analogously useful in isolating further ligands and variants thereof. Diagnostic and therapeutic uses of antibodies, binding fragments thereof, immunotoxins and idiotypic antibodies are described in Section VII, infra.

V. ACT-4 Ligands

The term ACT-4 ligand is used to denote a protein that specifically binds to an ACT-4 receptor polypeptide and that is capable of forming a complex with such a polypeptide, at least in part, by noncovalent binding. Ligands can be naturally-occurring or synthetic molecules, and can be in soluble form or anchored to the surface of a cell. Multiple different ligands may bind the same ACT-4 receptor. Conversely, one ligand may bind to more than one ACT-4 receptor. The term "ACT-4 ligand" does not usually include antibodies to ACT-4 receptor polypeptides. Usually, binding of a ligand to an ACT-4 receptor will initiate a signal that alters the physical and/or functional phenotype of a cell bearing the ACT-4 receptor and/or a cell bearing the ACT-4 ligand. Antibodies against either ACT-4 or its ligands can have the capacity to block or stimulate signal transduction. It will, of course, be recognized the designation of ACT-4 as a receptor and its specific binding partner as a ligand is somewhat arbitrary and might, in some circumstances, be reversed.

ACT-4 ligands are expected to share some of the properties of other ligands which bind to members of the nerve growth factor receptor superfamily. These ligands include the cytokines TNF-α, TNF-β, CD40-L, CD-27-L and CD30-L. With the exception of TNF-β, these ligands exist both as type II integral membrane cell surface proteins and as soluble proteins. The extracellular domains of these ligands consist of about 150 amino acids and form several β-pleated sheets, which assemble into a slitted cylindrical structure (termed a "jelly role" by Bazan et al., *Current Biology* 3:603–606 (1993)) (incorporated by reference for all purposes).

Source materials for supplying ACT-4 ligands are identified by screening different cell types, particularly lymphoid and hematopoietic cells, bodily fluids and tissue extracts, with labelled ACT-4 receptor, preferably in soluble form, as a probe. Often, the ACT-4 receptor or a binding fragment thereof is fused to a second protein for purposes of screening. Particularly suitable are recombinant globulins formed by fusing the extracellular portion of ACT-4 to the constant region of an immunoglobulin heavy chain.

ACT-4 ligands are purified from cells or other biological materials identified by this screening method using techniques of classical protein chemistry. Such techniques include selective precipitation with such substances as ammonium sulfate, column chromatography, immunopurification methods, and others. See, e.g., R. Scopes, *Protein Purification: Principles and Practice* (Springer-Verlag, NY, 1982) (incorporated by reference for all purposes). Usually, purification procedures will include an affinity chromatography step in which an ACT-4 polypeptide or a binding fragment thereof is used as the immobilized reagent. ACT-4-constant regions can be conveniently immobilized by binding of the constant region moiety to protein A or G. ACT-4 ligands can also be purified using anti-idiotypic antibodies to ACT-4 receptors as the affinity reagent.

To determine the amino acid sequence or to obtain polypeptide fragments of the receptor, the receptor may be digested with trypsin. Peptide fragments may be separated by reversed-phase high performance liquid chromatography (HPLC) and analyzed by gas-phase sequencing. Other sequencing methods known in the art may also be used. The sequence data can be used to design degenerate probes for isolation of cDNA or genomic clones encoding ACT-4 ligands.

Alternatively, cDNA clones encoding ACT-4 ligands can be obtained by expression cloning. In this approach, a cDNA library is prepared from cells expressing an ACT-4 ligand (identified as discussed, supra). The library is expressed in appropriate cells (e.g., COS-7), and clones bearing the ACT-4 ligand are identified by screening with labelled ACT-4 or binding fragment thereof, optionally fused to a constant domain of an immunoglobulin heavy chain.

The ACT-4 ligands or their binding domains can be used to affinity purify respective ACT-4 receptors. ACT-4 ligands and binding fragments thereof are also useful as agonists or antagonists of ACT-4 ligand binding, and can be used in the therapeutic methods discussed in Section VII, infra. For membrane-bound ACT-4 ligands, binding fragments will comprise part of the extracellular domain of an ACT-4 receptor. ACT-4 ligands and fragments thereof are also useful in screening assays for identifying agonists and antagonists of ACT-4 and/or its ligand. ACT-4 ligands can be fused to other protein, such as toxins and immunoglobulin constant domains, as discussed, supra, for ACT-4 receptors.

VI. Screening for Agonists and Antagonists

ACT-4 receptor and ACT-4 ligand fragments, analogs thereof, antibodies and anti-idiotypic antibodies thereto, as well as other chemical or biological agents are screened for their ability to block or enhance binding of an ACT-4 ligand to its receptor. In addition, they are tested for their ability to stimulate or inhibit metabolic processes, such as DNA synthesis or protein phosphorylation in cells bearing either an ACT-4 receptor or an ACT-4 ligand anchored to their surfaces.

In some methods, the compound under test is screened for its ability to block or enhance binding of a purified binding fragment of an ACT-4 receptor (or fusion protein thereof) to a purified binding fragment of an ACT-4 ligand (or fusion protein thereof). In such experiments, either the receptor or ligand fragment is usually immobilized to a solid support. The test compound then competes with an ACT-4 ligand or receptor fragment (whichever is not attached to the support) for binding to the support. Usually, either the test compound or the competing ligand or receptor is labelled.

In other methods, either or both of the ACT-4 receptor and ligand, or binding fragments of these molecules, are expressed on a cell surface. For example, ACT-4-h-1 antigen is expressed from recombinant DNA in e.g., COS-7 cells (see Example 6). In these methods, the existence of agonism or antagonism is determined from the degree of binding between an ACT-4 receptor and its ligand that occurs in the presence of the test compound. Alternatively, activity of the test compound is assayed by measurement of $^3$H-thymidine incorporation into DNA or $^{32}$P incorporation into proteins in cells bearing an ACT-4 receptor and/or cells bearing an ACT-4 ligand.

Compounds that block ACT-4-induced DNA synthesis or protein phosphorylation are antagonists. Compounds that activate DNA synthesis or phosphorylation via interaction with an ACT-4 receptor or its ligand are agonists. Agonistic or antagonistic activity can also be determined from other functional or physical endpoints of leukocyte activation, or from clinically desirable or undesirable outcomes, such as cytolytic activity, or extravasation of leukocytes into tissues from blood vessels.

The ability of agents to agonize or antagonize T-cell proliferation in vitro can be correlated with the ability to affect the immune response in vivo. In vivo activity is typically assayed using suitable animal models such as mice or rats. To assay the effect of agents on allograft rejection, for example, potential therapeutic agents can be administered to the animals at various times before introduction of the allogeneic tissue; and the animals can be monitored for graft rejection. Suitable methods for performing the transplant and monitoring for graft rejection have been described (see, e.g., Hislop et al., *J. Thorac. Cardiovasc.* 100:360–370 (1990)) (incorporated by reference for all purposes).

VII. Therapeutic and Diagnostic Methods and Compositions

A. Diagnostic Methods

Diseases and conditions of the immune system associated with an altered abundance, or functional mutation, of an ACT-4 receptor or its mRNA, or an ACT-4 ligand or its mRNA may be diagnosed using the probes and/or antibodies of the present invention. The provision of antibodies against the ACT-4 receptor and nucleic acid probes complementary to its mRNA allows activated CD4$^+$ T-cells to be distinguished from other leukocyte subtypes. The presence of such cells is indicative of a MHC class II induced immune response against, e.g., invading bacteria. Comparison of the numbers of activated CD4$^+$ cells and CD8$^+$ cells may allow differential diagnosis between bacterial and viral infections, which predominantly induce these respective activated cell types. The presence of activated CD4$^+$ cells is also indicative of undesirable diseases and conditions of the immune system, such as allograft rejection, graft versus host disease, autoimmune diseases, allergies and inflammation. The efficacy of therapeutic agents in treating such diseases and conditions can be monitored.

Diagnosis can be accomplished by removing a cellular sample (e.g., blood sample, lymph node biopsy or tissue) from a patient. The sample is then subjected to analysis for determining: (1) the amount of expressed ACT-4 receptor or ligand in individual cells of the sample (e.g., by immunohistochemical staining of fixed cells with an antibody or FACS™ analysis), (2) the amount of ACT-4 receptor or ligand mRNA in individual cells (by in situ hybridization with a labelled complementary polynucleotide probe), (3) the amount of ACT-4 receptor or ligand mRNA in the cellular sample by RNA extraction followed by hybridization to a labeled complementary polynucleotide probe (e.g., by Northern blotting, dot blotting, solution hybridization or quantitative PCR), or (4) the amount of ACT-4 receptor or ligand in the cellular sample (e.g., by cell disruption followed by immunoassay or Western blotting of the resultant cell extract).

Diagnosis can also be achieved by in vivo administration of a diagnostic reagent (e.g., a labelled anti-ACT-4 receptor antibody for diagnosis of activated $CD4^+$ T-cells) and detection by in vivo imaging. The concentration of diagnostic agent administered should be sufficient that the binding to those cells having the target antigen is detectable compared to the background signal. Further, it is desirable that the diagnostic reagent can be rapidly cleared from the circulatory system in order to give the best target-to-background signal ratio. The diagnostic reagent can be labelled with a radioisotope for camera imaging, or a paramagnetic isotope for magnetic resonance or electron spin resonance imaging.

A change (typically an increase) in the level of protein or mRNA of an ACT-4 receptor or ligand in a cellular sample from an individual, which is outside the range of clinically established normal levels, may indicate the presence of an undesirable immune reaction in the individual from whom the sample was obtained, and/or indicate a predisposition of the individual for developing (or progressing through) such a reaction. Protein or mRNA levels may be employed as a differentiation marker to identify and type cells of certain lineages (i.e., activated $CD4^+$ cells for the ACT-4 receptor) and developmental origins. Such cell-type specific detection may be used for histopathological diagnosis of undesired immune responses.

B. Diagnostic Kits

In another aspect of the invention, diagnostic kits are provided for the diagnostic methods described supra. The kits comprise container(s) enclosing the diagnostic reagents, such as labelled antibodies against ACT-4 receptors, and reagents and/or apparatus for detecting the label. Other components routinely found in such kits may also be included together with instructions for performing the test.

C. Pharmaceutical Compositions

The pharmaceutical compositions used for prophylactic or therapeutic treatment comprise an active therapeutic agent, for example, an ACT-4 receptor, ligand, fragments thereof, and antibodies and idiotypic antibodies thereto, and a variety of other components. The preferred form depends on the intended mode of administration and therapeutic application. The compositions may also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

D. Therapeutic Methods

The therapeutic methods employ the therapeutic agents discussed above for treatment of various diseases in humans or animals, particularly vertebrate mammals. The therapeutic agents include ACT-4 receptors, binding fragments thereof, ACT-4 ligands, binding fragments thereof, anti-ACT-4 receptor and ligand antibodies and anti-idiotypic antibodies thereto, binding fragments of these antibodies, humanized versions of these antibodies, immunotoxins, and other agents discussed, supra. Some therapeutic agents function by blocking or otherwise antagonizing the action of an ACT-4 receptor with its ligand. Other therapeutic agents function by killing cells bearing a polypeptide against which the agent is targeted. For example, anti-ACT-4 receptor antibodies with effector functions or which are conjugated to toxins, radioisotopes or drugs are capable of selectively killing activated $CD4^+$ T-cells. Selective elimination of such cells is particularly advantageous because an undesirable immune response can be reduced or eliminated, while preserving a residual immune capacity in the form of inactivated $CD4^+$ cells and $CD8^+$ cells to combat invading microorganisms to which a patient may subsequently be exposed. Other therapeutic agents function as agonists of the interaction between the ACT-4 receptor and ligand.

1. Dosages and Methods of Administration

In therapeutic applications, a pharmaceutical composition (e.g., comprising an anti-ACT-4 receptor antibody) is administered, in vivo or ex vivo, to a patient already suffering from an undesirable immune response (e.g., transplant rejection), in an amount sufficient to cure, partially arrest, or detectably slow the progression of the condition, and its complications. An amount adequate to accomplish this is defined as a "therapeutically effective dose" or "efficacious dose." Amounts effective for this use will depend upon the severity of the condition, the general state of the patient, and the route of administration, and combination with other immunosuppressive drugs, if any, but generally range from about 10 ng to about 1 g of active agent per dose, with single dosage units of from 10 mg to 100 mg per lo patient being commonly used. Pharmaceutical compositions can be administered systemically by intravenous infusion, or locally by injection. The latter is particularly useful for localized undesired immune response such as host versus graft rejection. For a brief review of methods for drug delivery, see Langer, *Science* 249:1527–1533 (1990) (incorporated by reference for all purposes).

In prophylactic applications, pharmaceutical compositions are administered to a patients at risk of, but not already suffering an undesired immune reaction (e.g., a patient about to undergo transplant surgery). The amount of antibody to be administered is a "prophylactically effective dose," the precise amounts of which will depend upon the patient's state of health and general level of immunity, but generally range from 10 ng to 1 g per dose, especially 10 mg to 100 mg per patient.

Because the therapeutic agents of the invention are likely to be more selective and generally less toxic than conventional immunomodulating agents, they will be less likely to cause the side effects frequently observed with the conventional agents. Moreover, because some of the therapeutic agents are human protein sequences (e.g., binding fragments of an ACT-4 receptor or ligand or humanized antibodies), they are less likely to cause immunological responses such as those observed with murine anti-CD3 antibodies. The therapeutic agents of the present invention can also be combined with traditional therapeutics, and can be used to lower the dose of such agents to levels below those associated with side effects. For example, other immunosuppressive agents such as antibodies to the α3 domain, T cell antigens (e.g., OKT4 and OKT3), antithymocyte globulin, as well as chemotherapeutic agents such as cyclosporine, glucocorticoids, azathioprine, prednisone can be used in conjunction with the therapeutic agents of the present invention.

For destruction of a specific population of target cells, it can be advantageous to conjugate the therapeutic agents of the present invention to another molecule. For example, the agents can be joined to liposomes containing particular immunosuppressive agents, to a specific monoclonal antibody or to a cytotoxin or other modulator of cellular activity, whereby binding of the conjugate to a target cell population will result in alteration of that population. A number of protein toxins have been discussed supra. Chemotherapeutic agents include, for example, doxorubicin, daunorubicin, methotrexate, cytotoxin, and anti-sense RNA. Antibiotics can also be used. In addition, radioisotopes such as yttrium-90, phosphorus-32, lead-212, iodine-131, or palladium-109 can be used. The emitted radiation destroys the targeted cells.

2. Diseases and Conditions Amenable to Treatment

The pharmaceutical compositions discussed above are suitable for treating several diseases and conditions of the immune system.

a. Transplant Rejection

Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individual from the same species), the host immune system is likely to mount an immune response to foreign antigens in the transplant (host-versus-graft disease) leading to destruction of the transplanted tissue. $CD8^+$ cells, $CD4^+$ cells and monocytes are all involved in the rejection of transplant tissues. The therapeutic agents of the present invention are useful to block alloantigen-induced immune responses in the donee (e.g., blockage or elimination of allogen-activation of $CD4^+$ T-cells by anti-ACT-4 receptor antibodies) thereby preventing such cells from participating in the destruction of the transplanted tissue or organ.

b. Graft Versus Host Disease

A related use for the therapeutic agents of the present invention is in modulating the immune response involved in "graft versus host" disease (GVHD). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used to block activation of, or eliminate, the donor T-cells (particularly activated $CD4^+$ T-cells, for therapeutic agents targeted against the ACT-4 receptor), thereby inhibiting their ability to lyse target cells in the host.

c. Autoimmune Diseases

A further situation in which immune suppression is desirable is in treatment of autoimmune diseases such as insulin-dependent diabetes mellitus, multiple sclerosis, stiff man syndrome, rheumatoid arthritis, myasthenia gravis and lupus erythematosus. In these disease, the body develops a cellular and/or humoral immune response against one of its own antigens leading to destruction of that antigen, and potentially crippling and/or fatal consequences. Activated $CD4^+$ T-cells are believed to play a major role in many autoimmune diseases. Autoimmune diseases are treated by administering one of the therapeutic agents of the invention, particularly agents targeted against an ACT-4 receptor. Optionally, the autoantigen, or a fragment thereof, against which the autoimmune disease is targeted can be administered shortly before, concurrently with, or shortly after the immunosuppressive agent. In this manner, tolerance can be induced to the autoantigen under cover of the suppressive treatment, thereby obviating the need for continued immunosuppression. See, e.g., Cobbold et al., WO 90/15152 (1990).

d. Inflammation

Inflammation represents the consequence of capillary dilation with accumulation of fluid and migration of phagocytic leukocytes, such as granulocytes and monocytes. Inflammation is important in defending a host against a variety of infections but can also have undesirable consequences in inflammatory disorders, such as anaphylactic shock, arthritis and gout. Activated T-cells have an important modulatory role in inflammation, releasing interferon γ and colony stimulating factors that in turn activate phagocytic leukocytes. The activated phagocytic leukocytes are induced to express a number of specific cells surface molecules termed homing receptors, which serve to attach the phagocytes to target endothelial cells. Inflammatory responses can be reduced or eliminated by treatment with the therapeutic agents of the present invention. For example, therapeutic agents targeted against the ACT-4 receptor function by blocking activation of, or eliminating activated, $CD4^+$ cells, thereby preventing these cells from releasing molecules required for activation of phagocytic cell types.

e. Infectious Agents

The invention also provides methods of augmenting the efficacy of vaccines in preventing or treating diseases and conditions resulting from infectious agents. Therapeutic agents having the capacity to activate CD4+ T-cells (e.g., certain monoclonal antibodies against a ACT-4-h-1 receptor polypeptide) are administered shortly before, concurrently with, or shortly after the vaccine containing a selected antigen. The therapeutic agent serves to augment the immune response against the selected antigen. These methods may be particularly advantageous in patients suffering from immune deficiency diseases.

The following examples are offered to illustrate, but not to limit, the invention.

EXAMPLES

Example 1

A Monoclonal Antibody Against ACT-4-h-1

Mice were immunized with PHA-transformed T-lymphoblasts. Splenocytes from immunized mice were fused with SP2/O myeloma cells and hybridomas secreting antibodies specific for the T-cell clone were selected. The hybridomas were cloned by limiting dilution. A monoclonal antibody, designated L106, produced by one of the resulting hybridoma, was selected for further characterization. The L106 antibody was found to have an IgG1 isotype. A hybridoma producing the antibody, designated HBL106 has been deposited at the American Type Culture Collection at Rockville, Md. 20852 USA, on Nov. 3, 1993, and assigned ATCC Accession No. HB 11483.

Example 2

Cellular Distribution of Polypeptide Recognized by L106 Antibody

Samples containing the antibody L106 were made available to certain participants at the Fourth International Workshop and Conference on Human Leucocyte Differentiation Antigens (Vienna 1989) for the purpose of identifying tissue and cell types which bind to the L106 antibody. The data from the workshop are presented in *Leukocyte Typing IV* (ed. W. Knapp, Oxford U. Press, 1989) (incorporated by reference for all purposes) and an accompanying computer data base available from Walter R. Gilks, MRC Biostatistics Unit, Cambridge University, England. This reference reports the L106 antibody binds a polypeptide of about 50 kDa. This polypeptide was reported to be present on HUT-102 cells (a transformed T-cell line), PHA-activated peripheral blood lymphocytes, an EBV-transformed B-lymphoid cell line, and HTLV-II transformed T-cell line, PMA-activated tonsil cells, ConA- or PHA-activated PBLs, and PMA-activated monocytes. The polypeptide was reported to be substantially absent on inter alia resting basophils, endothelial cells, fibroblasts, interferon γ-activated monocytes, peripheral non-T-cells, peripheral granulocytes, peripheral monocytes, peripheral mononuclear cells, peripheral T cells, and peripheral red blood cells.

The present inventors have obtained data indicating that the 50 kDa polypeptide (hereinafter "ACT-4-h-1 receptor") is preferentially expressed on the $CD4^+$ subspecies of activated T-cells. In one series of experiments, cell-specific ACT-4-h-1 expression was analyzed on unfractionated PBLs by a two-color staining method. PBL were activated with PHA for about two days (using the culture conditions described in Example 3), and analyzed for cell-surface expression of ACT-4-h-1 on different cellular subtypes by staining with two differently-labelled antibodies (FITC and PE labels). Labels were detected by FACS™ analysis essentially as described by Picker et al., *J. Immunol.* 150:1105–1121 (1993) (incorporated by reference for all purposes). One antibody, L106, was specific for ACT-4-h-1, the other antibody was specific for a particular leukocyte subtype. FIG. 1 shows three charts in which L106 staining is shown on the Y-axis of each chart, and anti-CD4, anti-CDB and anti-CD19 staining as the X-axes of the respective charts. For the chart stained with anti-CD4, many cells appear as double positives (i.e., express both CD4 and ACT-4-h-1). For the chart stained with anti-CD8, far fewer cells appear as double positives. For the chart stained with anti-CD19 (a B-cell marker), double-positive cells are substantially absent.

In another series of experiments expression of ACT-4-h-1 was analyzed by single-color staining on isolated cell types. Cells were stained with fluorescently labelled L106 antibody and the label was detected by FACS™ analysis. See Engleman et al., *J. Immuunol.* 127:2124–2129 (1981) (incorporated by reference for all purposes). In some experiments, cells were activated by PHA stimulation for about two days (again using the culture conditions described in Example 3). The results from this experiment, together with those from the two-color staining experiment described supra, are summarized in Table 1. Table 1 shows that about 80% of activated $CD4^+$ cells expressed ACT-4-h-1 with a mean channel fluorescence of >20, irrespective whether the $CD4^+$ cells are isolated (one-color staining) or in unfractionated PBLs (two-color staining). The level of expression of ACT-4-h-1 on activated $CD8^+$ cells is much lower than on activated CD4+ T-cells in the two-color staining experiment, and very much lower in the one-color staining. Thus, the extent of expression on activated $CD8^+$ cells appears to depend on whether the C8+ cells are fractionated from other PBLs before activation. In unfractionated $CD8^+$ cells (two-color staining), about 10% of cells express ACT-4-h-1, with a mean channel fluorescence of about 4. In the fractionated cells, only about 4% of cells express ACT-4-h-1 with a mean channel fluorescence of about 2. These data suggest that ACT-4-h-1 is expressed only on a small subtype of activated $CD8^+$ cells and that this subtype is somewhat more prevalent when the $CD8^+$ cells are activated in the presence of other PBLs.

Table 1 also indicates that ACT-4-h-1 was substantially absent on all resting leukocyte subtypes tested (i.e., $CD4^+$ T-cells, $CD8^+$ T-cells, $CD19^+$ B-cells, $CD14^+$ monocytes, granulocytes and platelets), and was also substantially absent on activated B-cells and monocytes. ACT-4-h-1 was also found to be substantially absent on most tumor cell lines tested. However, Molt3, Raji and NC37 cell lines did show a low level of expression.

TABLE 1

CELL SPECIFICITY OF ACT-4-h-1 EXPRESSION

| | Expression of ACT-4-h-1 | |
|---|---|---|
| | % Cells | MCF[1] |
| Two Color Staining | | |
| $CD4^+$ T-Cells (resting) | <2 | <2 |
| $CD4^+$ T-Cells (activated)[2] | 80 | 25 |
| $CD8^+$ T-Cells (resting) | <2 | <2 |
| $CD8^+$ T-Cells (activated) | 10 | 4 |
| $CD19^+$ B-Cells (resting) | <2 | <2 |
| $CD19^+$ B-Cells (activated) | <2 | <2 |
| $CD14^+$ Monocytes (resting) | <2 | <2 |
| $CD14^+$ Monocytes (activated) | <2 | <2 |
| One Color Staining | | |
| PBLs (resting) | <2 | 3 |
| PBLs (activated) | 50 | 27 |
| $CD4^+$ (resting) | <2 | <2 |
| $CD4^+$ (activated) | 80 | 22 |
| $CD8^+$ (resting) | <2 | <2 |
| $CD8^+$ (activated) | 4 | 2 |
| Granulocytes | <2 | <2 |
| Platelets | <2 | <2 |
| Tumor Lines | | |
| Molt-4, CEM, Hut 78, H9, Jurkat | <2 | <2 |

TABLE 1-continued

CELL SPECIFICITY OF ACT-4-h-1 EXPRESSION

| | Expression of ACT-4-h-1 | |
|---|---|---|
| | % Cells | MCF[1] |
| HPB-ALL, Sezary, T-AU | <2 | <2 |
| Molt-3 | 20 | 3 |
| B-LCL, Arent, RML, JY, KHY, PGf | <2 | <2 |
| MSAB, CESS, 9037, 9062 | <2 | <2 |
| Dandi, Ramos, Namalwa | <2 | <2 |
| Raji, NC37 | 30 | 4 |
| U937, THP-1, HL-60 | <2 | <2 |
| Kgla, K562, HEL | <2 | <2 |

[1] MCF = Mean Channel Fluorescence.
[2] Cells indicated as "activated" had been stimulated with PHA for about three days.

Example 3

Time Course of ACt-4-h-1 Expression Responsive to CD4+ T-cell Activation

CD4+ T-cells were tested for expression of ACT-4-h-1 receptors in response to various activating stimuli. CD4+ T-cells were purified from peripheral blood mononuclear cells by solid-phase immunoadsorption ("panning"). $5 \times 10^4$ CD4+ T-cells were cultured with an activating agent in microtiter wells containing RPMI medium supplemented with 10% human serum. Three different activating agents were used: (1) $5 \times 10^4$ irradiated (3000 rads) monocytes, (2) PHA (1 µg/ml) and (3) tetanus toxoid (5 µg/ml). $^3$H-thymidine was added to the cultures 12–16 h before harvest. After harvest, cells were tested for the expression of cell surface antigens by incubation with various labelled antibodies (L106, anti-CD4 and anti-CD8), as described by Engleman et al., *J. Immunol.* 127:2124–2129 (1981).

FIG. 2 shows the appearance of ACT-4-h-1 in response to alloantigen activation. Before activation, no expression was observed. The percentage of cells expressing the ACT-4-h-1 receptor increases with time, peaking at about 30% after about seven days of alloantigen activation. The results also show that essentially all cells expressing ACT-4-h-1 also expressed the CD4 receptor and that essentially no such cells expressed the CD8 receptor. FIG. 3 presents similar data for the appearance of ACT-4-h-1 in response to tetanus toxoid activation. Again, the percentage of cells expressing ACT-4-h-1 peaked at about seven days. However, at this time a higher percentage of cells (about 60%) expressed the receptor. FIG. 4 presents similar data for the appearance of ACT-4-h-1 on CD4+ T-cells in response to PHA activation. In this situation, the percentage of CD4+ T-cells expressing the receptor peaks at about 65% after three days of activation.

It is concluded that ACT-4-h-1 is a CD4+ T-cell activation antigen that is expressed in response to diverse activating stimuli.

Example 4

Cloning ACT-4-h-1 cDNA

The cDNA clone for the ACT-4-h-1 receptor was isolated using a slightly modified COS cell expression system, first developed by Aruffo & Seed, supra. RNA was isolated from 72-hour PHA activated human peripheral blood lymphocytes. Total RNA was extracted with TRI-reagent (Molecular Research Center), and poly(A)+RNA was isolated by oligo dT-magnetic bead purification (Promega). cDNA was synthesized by the method of Gubler & Hoffman, *Gene* 25:263–369 (1982) using superscript reverse transcriptase (Gibco/BRL) and an oligo dT primer. The blunted cDNA was ligated to non-self-complementary BstX1 adaptors and passed over a sephacryl S-400 spin column to remove unligated adaptors and small fragments (<300 base pairs). The linkered cDNA was then ligated into a BstX1 cut eukaryotic expression vector, pcDNA-IRL, an ampicillin resistant version of pcDNA-I(Invitrogen). The precipitated and washed products of the ligation reaction were electroporated into *E. coli* strain WM1100(BioRad). Plating and counting of an aliquot of the transformed bacteria revealed a total count of 2 million independent clones in the unamplified library. Average insert size was determined to be 1.2 kb. The bulk of the library was amplified in liquid culture, 250 ml standard LB media. Plasmid was recovered by alkaline lysis and purified over an ion-exchange column (Qiagen).

Sub-confluent COS-7 cells were transfected with the purified plasmid DNA by electroporation. Cells were plated on 100 mm dishes and allowed to grow for 48 hours. Cells were recovered from the plates with PBS-EDTA solution, incubated with monoclonal antibody L106, and were panned according to standard procedures. A second round panning revealed enrichment as numerous COS cells adsorbed to the plates. Episomal DNA was recovered from the immunoselected cells by the Hirt method, and electroporated into bacteria for amplification.

Bacteria transformed with plasmid from the second round Hirt preparation were diluted into small pools of about 100 colonies. The pools were amplified and their DNA purified and tested for the ability to confer expression of the L106 antigen on COS-7 cells by immunofluorescence. Phycoerythrin-conjugated L106 antibody was used to stain COS-7 cell monolayers and the cells were then examined by manual immunofluorescence microscopy. Miniprep DNA from four out of eight pools was positive when tested for expression. The pool with the best expression, pool E, was divided into smaller pools of 12 colonies. Three out of eight sub-pools were positive, and sub-pool E1 was plated to allow for the analysis of single colonies. Clone E1-27 was found to confer high level expression of ACT-4-h-1 receptor on the surface of transfected COS cells.

Example 5 cDNA Sequence Analysis

The insert from the clone designated E1-27 was subcloned into pBluescript and sequenced by the dideoxy chain termination method, using the T7 polymerase autoread sequencing kit (Pharmacia) on an ALF sequencer (Pharmacia). Restriction mapping revealed several convenient sites for subcloning. Five subclones were generated in pBluescript and were sequenced on both strands with M13 forward and universal primers.

The cDNA and deduced amino acid sequences of ACT-4-h-1 are shown in FIG. 5. The ACT-4-h-1 cDNA sequence of 1,137 base pairs contains a 14-bp 5' untranslated region and a 209-bp 3' untranslated region. An AATAAA polyadenylation signal is present at position 1,041 followed by an 80-bp poly A tail starting at position 1,057. The longest open reading frame begins with the first ATG at position 15 and ends with a TGA at position 846. The predicted amino acid sequence is that of a typical type 1 integral membrane protein. Hydrophobicity analysis reveals a putative signal sequence following the initiating ATG, with a short stretch of basic residues followed by a longer stretch of hydrophobic residues. A predicted signal peptide cleavage site is present at residue 22 or 24 (the latter being the more likely by the criteria of von Heijne, *Nucleic Acids Res.* 14, 4683–4690 (1986)) (incorporated by reference for all purposes), leaving a mature protein of 253 amino acid residues (or 255 amino acids, if cleavage occurs at the less probable site). Hydrophobicity analysis also reveals a single large stretch of 27 hydrophobic residues predicted to be the transmembrane domain, which predicts an extracellular domain of 189 (or 191) amino acids and an intracellular domain of 37 amino acids. The extracellular domain is cysteine rich, where 18 cysteines are found within a stretch of 135 amino acids. The predicted molecular mass (Mr) for the mature protein is 27,400, and there are two potential N-glycosylation sites at amino acid residues 146 and 160.

Comparison of the amino acid sequence of ACT-4-h-1 with known sequences in the swiss-prot database using the BLAZE program reveals a sequence similarity with members of the nerve growth factor receptor superfamily. Amino acid sequences are at least 20% identical for NGF-R, TNF-R, CD40, 41-BB, and fas/APO-1, and 62% for OX-40, allowing for gaps and deletions. Alignments of the various proteins reveal the conservation of multiple cysteine rich motifs. Three of these motifs are present in ACT-4-h-1 and OX-40, compared with four such motifs in NGF-R and CD40.

Comparison of the nucleotide sequence of ACT-4-h-1 with known sequences in the Genbank and EMBL databases using the programs BLAST and FASTDB revealed a high degree of sequence similarity with only one member of the nerve growth factor receptor family, OX-40. Allowing for gaps and insertions, the sequence identity is 66%. Comparison of the ACT-4-h-1 and OX-40 nucleotide sequences reveals that both contain a 14-bp 5' untranslated region, and both contain approximately 80-bp poly A tails. In ACT-4-h-1, however, there is a slight lengthening of the 3' untranslated region from 187-bp to 209-bp, and there is a lengthening of the coding region from 816-bp to 834-bp, a difference of 18-bp or 6 amino acid insertions. Aligning the two amino acid sequences reveals that four of the amino acid insertions occur prior to the signal sequence cleavage site. Thus, the mature ACT-4-h-1 receptor protein contains one more amino acid residue than OX-40 (i.e., 253 vs. 252 amino acids). Remarkably, the ACT-4-h-1 nucleotide sequence is much more GC rich, than the OX-40 sequence (70% v. 55%) indicating that the two sequences will not hybridize under stringent conditions.

Example 6

Production of Stable ACT-4-h-1 Transfectants

An XbaI-HindIII fragment was excised from the construct described in Example 4, and inserted into XbaI/HindIII-digested pcDNA-I-neo (Invitrogen) to generate an expression vector termed ACT-4-h-1-neo (FIG. 6). This vector was linearized with Sf1 and electroporated into three eukaryotic cell lines. These cell lines were SP2/O (a mouse myeloma derived from the Balb/c strain), Jurkat (a transformed human T-cell line) and COS-7 (an adherent monkey cell line). After a 48-h recovery period, transformed cells were selected in 1 mg/ml G418 (Gibco). After three weeks of selection, neo-resistant cell lines were incubated with a saturating concentration of L106 antibody, washed and overlayered onto 100 mm petri dishes coated with goat anti-mouse IgG to select for cells expressing ACT-4-h-1. After washing off unbound cells, adherent cells were recovered and expanded in tissue culture. Cell lines were subject to two further rounds of panning and expression. The resulting cell lines were shown by direct immunofluorescence staining to express abundant STAN-4-h-1 (FIG. 7).

Example 7

Production of an ACT-4-h-1-Immunoglobulin Fusion Protein

A soluble fusion protein has been constructed in which the extracellular domain of ACT-4-h-1 is linked via its C-terminal to the N-terminal of the constant domain of a human immunoglobulin. The vector encoding ACT-4-h-1 described in Example 4 was cleaved with SmaI and NotI to excise all ACT-4-h-1 sequences downstream of the SmaI site including the transmembrane, cytoplasmic and 3' untranslated regions. The remaining region encodes the soluble extracellular portion of ACT-4-h-1 (FIG. 8). The source of the immunoglobulin constant region to be joined to the ACT-4-h-1 extracellular domain was a plasmid termed 5K-41BB-Eg1 (*Proc. Natl. Acad. Sci. (USA)* 89:10360–10364) (incorporated by reference for all purposes). This plasmid contains a 1.3 kb BamHI/EagI genomic fragment encoding the hinge, CH2 and terminal CH3 domains of human Ig, isotype gamma 1. The fragment required modification for insertion into the SmaI/NotI ends of the ACT-4-h-1 vector, while preserving the peptide reading frame across the SmaI junction to be formed by blunt-end ligation. The vector 5k-41BB-Eg1 was cut with BamH1 and the resulting 5' extensions were filled with Klenow fragment. The vector was then cut with EagI releasing the 1.3 kb fragment with blunt and NotI compatible ends. This fragment was ligated with SmaI/NotI digested ACT-4-h-1 vector. The ligation mix was electroporated into *E. coli* and multiple transformant clones screened with PCR using ACT-4-h-1 and IgG1 nucleotide fragments as primers.

Plasmids containing the ACT-4-h-1-IgG1 coding were electroporated into COS cells. The cells were allowed to grow for five days at which point their supernatants were harvested and sterile filtered through a 0.2 micron membrane. The supernatants were tested for expression of ACT-4-h-1-IgG1 by dot blotting. Supernatants were blotted onto Nitrocellulose and blocked with 5% nonfat dry milk. Replica blots were probed with antibody L106 or alkaline phosphatase-labelled goat anti-human immunoglobulin IgG (American Qualex). Antibody L106 was detected with an alkaline phosphatase labelled goat anti-mouse IgG. NBT/BCIP (Pierce) was used as a calorimetric substrate. High producing positive clones were sequenced at the junction site to confirm proper vector construction. The resulting fusion gene is depicted in FIG. 9.

For the purposes of clarity and understanding, the invention has been described in these examples and the above disclosure in some detail. It will be apparent, however, that certain changes and modifications may be practiced within the scope of the appended claims. All publications and patent applications are hereby incorporated by reference for all purposes to the same extent as if each were individually denoted as being incorporated by reference.

What is claimed is:

1. An isolated ACT-4 receptor polypeptide comprising an amino acid sequence selected from the group consisting of:
   (a) the amino acid sequence of the ACT-4-h-1 receptor polypeptide shown in FIG. 5 (SEQ ID NO:2);
   (b) variants of the amino acid sequence of (a) having at least one conservative amino acid substitution; and
   (c) variants of the amino acid sequence of (a) encoded by a nucleic acid which hybridizes under stringent conditions to a nucleic acid encoding the amino acid sequence of (a), said variants of (b) and (c) having the ability to bind specifically to antibody L106.

2. The isolated ACT-4 receptor polypeptide of claim 1 consisting of the amino acid sequence of the ACT-4-h-1 receptor polypeptide shown in FIG. 5 (SEQ ID NO:2).

3. The isolated ACT-4 receptor polypeptide of claim 1 that is human.

4. An isolated ACT-4 receptor soluble polypeptide comprising an amino acid sequence selected from the group consisting of:
   (a) the amino acid sequence of the extracellular domain of the ACT-4-h-1 receptor polypeptide shown in FIG. 5 (SEQ ID NO:2), said extracellular domain having an amino terminus of any amino acid 1 to 25 of the amino acid sequence shown in FIG. 5 (SEQ ID NO:2) and a carboxyl terminus of amino acid 213 of the amino acid sequence shown in FIG. 5 (SEQ ID NO:2);
   (b) variants of the amino acid sequence of (a) having at least one conservative amino acid substitution; and
   (c) variants of the amino acid sequence of (a) encoded by a nucleic acid which hybridizes under stringent conditions to a nucleic acid encoding the amino acid sequence of (a), said variants of (b) and (c) having the ability to bind specifically to antibody L106.

5. The isolated ACT-4 receptor soluble polypeptide of claim 4 which is fused to a heterologous polypeptide.

6. The isolated ACT-4 receptor soluble polypeptide of claim 5 wherein the heterologous polypeptide is selected from the group consisting of a chromogenic enzyme, protein A, protein G, a FLAG protein, a toxin and a component of an immunoglobulin.

7. The isolated ACT-4 receptor soluble polypeptide of claim 5 wherein the heterologous polypeptide comprises a constant region domain of an immunoglobulin heavy chain.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 1057 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i x ) FEATURE:
( A ) NAME/KEY: CDS
( B ) LOCATION: 15..845
( D ) OTHER INFORMATION: /standard_name= "ACT-4 cDNA"

( x i ) SEQUENCE DESCRIPTION: SEQ ID NO:1:

```
CAGCAGAGAC GAGG ATG TGC GTG GGG GCT CGG CGG CTG GGC CGC GGG CCG        50
              Met Cys Val Gly Ala Arg Arg Leu Gly Arg Gly Pro
                1           5                      10

TGT GCG GCT CTG CTC CTC CTG GGC CTG GGG CTG AGC ACC GTG ACG GGG        98
Cys Ala Ala Leu Leu Leu Leu Gly Leu Gly Leu Ser Thr Val Thr Gly
         15                  20                  25

CTC CAC TGT GTC GGG GAC ACC TAC CCC AGC AAC GAC CGG TGC TGC CAC       146
Leu His Cys Val Gly Asp Thr Tyr Pro Ser Asn Asp Arg Cys Cys His
     30                  35                  40

GAG TGC AGG CCA GGC AAC GGG ATG GTG AGC CGC TGC AGC CGC TCC CAG       194
Glu Cys Arg Pro Gly Asn Gly Met Val Ser Arg Cys Ser Arg Ser Gln
 45                  50                  55                  60

AAC ACG GTG TGC CGT CCG TGC GGG CCG GGC TTC TAC AAC GAC GTG GTC       242
Asn Thr Val Cys Arg Pro Cys Gly Pro Gly Phe Tyr Asn Asp Val Val
                 65                  70                  75

AGC TCC AAG CCG TGC AAG CCC TGC ACG TGG TGT AAC CTC AGA AGT GGG       290
Ser Ser Lys Pro Cys Lys Pro Cys Thr Trp Cys Asn Leu Arg Ser Gly
             80                  85                  90

AGT GAG CGG AAG CAG CTG TGC ACG GCC ACA CAG GAC ACA GTC TGC CGC       338
Ser Glu Arg Lys Gln Leu Cys Thr Ala Thr Gln Asp Thr Val Cys Arg
         95                 100                 105

TGC CGG GCG GGC ACC CAG CCC CTG GAC AGC TAC AAG CCT GGA GTT GAC       386
Cys Arg Ala Gly Thr Gln Pro Leu Asp Ser Tyr Lys Pro Gly Val Asp
    110                 115                 120

TGT GCC CCC TGC CCT CCA GGG CAC TTC TCC CCA GGC GAC AAC CAG GCC       434
Cys Ala Pro Cys Pro Pro Gly His Phe Ser Pro Gly Asp Asn Gln Ala
125                 130                 135                 140

TGC AAG CCC TGG ACC AAC TGC ACC TTG GCT GGG AAG CAC ACC CTG CAG       482
Cys Lys Pro Trp Thr Asn Cys Thr Leu Ala Gly Lys His Thr Leu Gln
                145                 150                 155

CCG GCC AGC AAT AGC TCG GAC GCA ATC TGT GAG GAC AGG GAC CCC CCA       530
Pro Ala Ser Asn Ser Ser Asp Ala Ile Cys Glu Asp Arg Asp Pro Pro
            160                 165                 170

GCC ACG CAG CCC CAG GAG ACC CAG GGC CCC CCG GCC AGG CCC ATC ACT       578
Ala Thr Gln Pro Gln Glu Thr Gln Gly Pro Pro Ala Arg Pro Ile Thr
        175                 180                 185

GTC CAG CCC ACT GAA GCC TGG CCC AGA ACC TCA CAG GGA CCC TCC ACC       626
Val Gln Pro Thr Glu Ala Trp Pro Arg Thr Ser Gln Gly Pro Ser Thr
    190                 195                 200

CGG CCC GTG GAG GTC CCC GGG GGC CGT GCG GTT GCC GCC ATC CTG GGC       674
```

```
Arg  Pro  Val  Glu  Val  Pro  Gly  Gly  Arg  Ala  Val  Ala  Ala  Ile  Leu  Gly
205                 210                      215                           220

CTG  GGC  CTG  GTG  CTG  GGG  CTG  CTG  GGC  CCC  CTG  GCC  ATC  CTG  CTG  GCC       722
Leu  Gly  Leu  Val  Leu  Gly  Leu  Leu  Gly  Pro  Leu  Ala  Ile  Leu  Leu  Ala
                    225                      230                           235

CTG  TAC  CTG  CTC  CGG  AGG  GAC  CAG  AGG  CTG  CCC  CCC  GAT  GCC  CAC  AAG       770
Leu  Tyr  Leu  Leu  Arg  Arg  Asp  Gln  Arg  Leu  Pro  Pro  Asp  Ala  His  Lys
                    240                      245                 250

CCC  CCT  GGG  GGA  GGC  AGT  TTC  CGG  ACC  CCC  ATC  CAA  GAG  GAG  CAG  GCC       818
Pro  Pro  Gly  Gly  Gly  Ser  Phe  Arg  Thr  Pro  Ile  Gln  Glu  Glu  Gln  Ala
               255                 260                      265

GAC  GCC  CAC  TCC  ACC  CTG  GCC  AAG  ATC  TGACCTGGGC  CCACCAAGGT                   865
Asp  Ala  His  Ser  Thr  Leu  Ala  Lys  Ile
          270                 275

GGACGCTGGG  CCCCGCCAGG  CTGGAGCCCG  GAGGGTCTGC  TGGGCGAGCA  GGGCAGGTGC                925

AGGCCGCCTG  CCCCGCCACG  CTCCTGGGCC  AACTCTGCAC  CGTTCTAGGT  GCCGATGGCT                985

GCCTCCGGCT  CTCTGCTTAC  GTATGCCATG  CATACCTCCT  GCCCCGCGGG  ACCACAATAA               1045

AAACCTTGGC  AG                                                                       1057
```

( 2 ) INFORMATION FOR SEQ ID NO:2:

( i ) SEQUENCE CHARACTERISTICS:
        ( A ) LENGTH: 277 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Cys  Val  Gly  Ala  Arg  Arg  Leu  Gly  Arg  Gly  Pro  Cys  Ala  Ala  Leu
1                   5                        10                      15

Leu  Leu  Leu  Gly  Leu  Gly  Leu  Ser  Thr  Val  Thr  Gly  Leu  His  Cys  Val
               20                  25                       30

Gly  Asp  Thr  Tyr  Pro  Ser  Asn  Asp  Arg  Cys  Cys  His  Glu  Cys  Arg  Pro
               35                  40                       45

Gly  Asn  Gly  Met  Val  Ser  Arg  Cys  Ser  Arg  Ser  Gln  Asn  Thr  Val  Cys
     50                       55                  60

Arg  Pro  Cys  Gly  Pro  Gly  Phe  Tyr  Asn  Asp  Val  Val  Ser  Ser  Lys  Pro
65                       70                  75                            80

Cys  Lys  Pro  Cys  Thr  Trp  Cys  Asn  Leu  Arg  Ser  Gly  Ser  Glu  Arg  Lys
                    85                       90                       95

Gln  Leu  Cys  Thr  Ala  Thr  Gln  Asp  Thr  Val  Cys  Arg  Cys  Arg  Ala  Gly
               100                 105                      110

Thr  Gln  Pro  Leu  Asp  Ser  Tyr  Lys  Pro  Gly  Val  Asp  Cys  Ala  Pro  Cys
          115                 120                      125

Pro  Pro  Gly  His  Phe  Ser  Pro  Gly  Asp  Asn  Gln  Ala  Cys  Lys  Pro  Trp
          130                 135                      140

Thr  Asn  Cys  Thr  Leu  Ala  Gly  Lys  His  Thr  Leu  Gln  Pro  Ala  Ser  Asn
145                      150                 155                           160

Ser  Ser  Asp  Ala  Ile  Cys  Glu  Asp  Arg  Asp  Pro  Pro  Ala  Thr  Gln  Pro
                    165                 170                      175

Gln  Glu  Thr  Gln  Gly  Pro  Pro  Ala  Arg  Pro  Ile  Thr  Val  Gln  Pro  Thr
               180                 185                      190

Glu  Ala  Trp  Pro  Arg  Thr  Ser  Gln  Gly  Pro  Ser  Thr  Arg  Pro  Val  Glu
          195                 200                      205

Val  Pro  Gly  Gly  Arg  Ala  Val  Ala  Ala  Ile  Leu  Gly  Leu  Gly  Leu  Val
          210                 215                      220
```

| | | | | | | | | | | | | | | |
|---|---|---|---|---|---|---|---|---|---|---|---|---|---|---|
| Leu 225 | Gly | Leu | Leu | Gly | Pro 230 | Leu | Ala | Ile | Leu | Leu 235 | Ala | Leu | Tyr | Leu | Leu 240 |
| Arg | Arg | Asp | Gln | Arg 245 | Leu | Pro | Pro | Asp | Ala 250 | His | Lys | Pro | Pro | Gly 255 | Gly |
| Gly | Ser | Phe | Arg 260 | Thr | Pro | Ile | Gln | Glu 265 | Glu | Gln | Ala | Asp | Ala 270 | His | Ser |
| Thr | Leu | Ala 275 | Lys | Ile | | | | | | | | | | | |